(12) United States Patent
To et al.

(10) Patent No.: US 9,913,736 B2
(45) Date of Patent: Mar. 13, 2018

(54) METHOD OF DISTRACTING AN INTERVERTEBRAL SPACE

(71) Applicant: INTEGRITY IMPLANTS INC., Jupiter, FL (US)

(72) Inventors: John To, Newark, CA (US); Praveen Gopal Rao, Newark, CA (US)

(73) Assignee: INTEGRITY IMPLANTS INC., Jupiter, FL (US)

( * ) Notice: Subject to any disclaimer, the term of this patent is extended or adjusted under 35 U.S.C. 154(b) by 242 days.

(21) Appl. No.: 14/622,864

(22) Filed: Feb. 14, 2015

(65) Prior Publication Data
US 2015/0157464 A1 Jun. 11, 2015

Related U.S. Application Data

(63) Continuation of application No. 14/480,416, filed on Sep. 8, 2014, now Pat. No. 8,986,387.
(Continued)

(51) Int. Cl.
*A61F 2/44* (2006.01)
*A61F 2/46* (2006.01)
(Continued)

(52) U.S. Cl.
CPC .......... *A61F 2/4684* (2013.01); *A61B 17/025* (2013.01); *A61F 2/442* (2013.01);
(Continued)

(58) Field of Classification Search
CPC .. A61F 2/44; A61F 2/46; A61F 2/4684; A61F 2/4455; A61F 2/4611; A61B 17/02
See application file for complete search history.

(56) References Cited

U.S. PATENT DOCUMENTS 4,309,777 A 1/1982 Patil
4,733,665 A 3/1988 Palmaz
(Continued)

FOREIGN PATENT DOCUMENTS

CN 101909548 7/2014
EP 1011503 2/1998
(Continued)

OTHER PUBLICATIONS

U.S. Appl. No. 61/737,054, To, filed Dec. 15, 2013.
(Continued)

*Primary Examiner* — Christopher Beccia
(74) *Attorney, Agent, or Firm* — Brian S. Boyer; Syndicated Law, PC

(57) ABSTRACT

Systems and methods for distracting an intervertebral disc space are provided. The systems use a staged, bilaterally expandable trial. The systems and methods of distracting an intervertebral space are provided in a manner that addresses the problem of subsidence. The method includes inserting the trial into the intervertebral space in a collapsed state and, once inserted, the trial is then used for distracting the intervertebral space using an expansion that includes a first stage and a second stage. The first stage includes expanding the trial laterally toward the peripheral zones of the top vertebral plate and the bottom vertebral plate, and the second stage includes expanding the trial vertically to distract the intervertebral space.

29 Claims, 11 Drawing Sheets

Related U.S. Application Data

(60) Provisional application No. 61/875,688, filed on Sep. 9, 2013.

(51) Int. Cl.
*A61B 17/02* (2006.01)
*A61F 2/30* (2006.01)

(52) U.S. Cl.
CPC .......... *A61F 2/4425* (2013.01); *A61F 2/4455* (2013.01); *A61F 2/4611* (2013.01); *A61B 2017/0256* (2013.01); *A61F 2002/30018* (2013.01); *A61F 2002/3055* (2013.01); *A61F 2002/30154* (2013.01); *A61F 2002/30163* (2013.01); *A61F 2002/30266* (2013.01); *A61F 2002/30545* (2013.01); *A61F 2002/30556* (2013.01); *A61F 2002/30563* (2013.01); *A61F 2002/30565* (2013.01); *A61F 2002/30579* (2013.01)

(56) References Cited

U.S. PATENT DOCUMENTS

| | | | |
|---|---|---|---|
| 4,759,766 A | 7/1988 | Buettner-Janz et al. | |
| 4,820,305 A | 4/1989 | Harms et al. | |
| 4,997,432 A | 3/1991 | Keller | |
| 5,192,327 A | 3/1993 | Brantigan | |
| 5,221,261 A | 6/1993 | Termin et al. | |
| 5,609,635 A | 3/1997 | Michelson | |
| 5,658,336 A | 8/1997 | Pisharodi | |
| 5,976,187 A | 11/1999 | Richelsoph | |
| 5,980,522 A | 11/1999 | Koros | |
| 5,980,552 A | 11/1999 | Pinchasik et al. | |
| 6,039,761 A | 3/2000 | Li et al. | |
| 6,102,950 A * | 8/2000 | Vaccaro | A61F 2/447 606/247 |
| 6,193,757 B1 | 2/2001 | Foley et al. | |
| 6,368,351 B1 | 4/2002 | Glenn et al. | |
| 6,375,682 B1 | 4/2002 | Fleischmann et al. | |
| 6,395,031 B1 | 5/2002 | Foley et al. | |
| 6,409,766 B1 | 6/2002 | Brett | |
| 6,419,705 B1 | 7/2002 | Erickson | |
| 6,432,107 B1 | 8/2002 | Ferree | |
| 6,443,989 B1 | 9/2002 | Jackson | |
| 6,482,235 B1 | 11/2002 | Lambrecht et al. | |
| 6,488,710 B2 | 12/2002 | Besselink | |
| 6,575,899 B1 | 6/2003 | Foley et al. | |
| 6,582,467 B1 | 6/2003 | Teitelbaum | |
| 6,595,998 B2 | 7/2003 | Johnson et al. | |
| 6,666,891 B2 | 12/2003 | Boehm, Jr. et al. | |
| 6,821,276 B2 | 11/2004 | Lambrecht et al. | |
| 6,893,464 B2 | 5/2005 | Kiester | |
| 7,018,415 B1 | 3/2006 | McKay | |
| 7,083,650 B2 | 8/2006 | Moskowitz et al. | |
| 7,087,055 B2 | 8/2006 | Lim et al. | |
| 7,214,243 B2 | 5/2007 | Taylor | |
| 7,217,293 B2 | 5/2007 | Branch | |
| 7,544,208 B1 | 6/2009 | Mueller et al. | |
| 7,621,950 B1 | 11/2009 | Globerman et al. | |
| 7,655,046 B2 | 2/2010 | Dryer et al. | |
| 7,678,148 B2 | 3/2010 | Peterman | |
| 7,771,473 B2 | 8/2010 | Thramann | |
| D626,233 S | 10/2010 | Cipoletti et al. | |
| 7,819,921 B2 | 10/2010 | Grotz | |
| 7,828,845 B2 | 11/2010 | Estes et al. | |
| 7,846,206 B2 | 12/2010 | Oglaza et al. | |
| 7,850,733 B2 | 12/2010 | Baynham et al. | |
| 7,862,618 B2 | 1/2011 | White et al. | |
| 7,879,098 B1 | 2/2011 | Simmons, Jr. | |
| 7,909,872 B2 | 3/2011 | Zipnick | |
| 8,062,375 B2 | 11/2011 | Glerum et al. | |
| 8,070,754 B2 | 12/2011 | Fabian et al. | |
| 8,070,813 B2 | 12/2011 | Grotz et al. | |
| 8,083,744 B2 | 12/2011 | Dorchak | |
| 8,088,163 B1 | 1/2012 | Kleiner | |
| 8,105,382 B2 | 1/2012 | Olmos et al. | |
| 8,110,004 B2 | 2/2012 | Valdevit et al. | |
| 8,123,755 B2 | 2/2012 | Johnson et al. | |
| 8,167,950 B2 | 5/2012 | Aferzon et al. | |
| 8,182,538 B2 | 5/2012 | O'Neil et al. | |
| 8,187,332 B2 | 5/2012 | McLuen | |
| 8,236,058 B2 | 8/2012 | Fabian et al. | |
| 8,241,363 B2 | 8/2012 | Sommerich et al. | |
| 8,267,939 B2 | 9/2012 | Cipoletti et al. | |
| 8,303,658 B2 | 11/2012 | Peterman | |
| 8,353,961 B2 | 1/2013 | McClintock | |
| 8,353,963 B2 | 1/2013 | Glerum | |
| 8,551,173 B2 | 10/2013 | Lechmann et al. | |
| 8,663,332 B1 | 3/2014 | To et al. | |
| 8,986,387 B1 | 3/2015 | To et al. | |
| 9,060,876 B1 | 6/2015 | To et al. | |
| 2002/0040243 A1 | 4/2002 | Attali | |
| 2002/0138146 A1 | 9/2002 | Jackson | |
| 2003/0074075 A1 | 4/2003 | Thomas et al. | |
| 2003/0083746 A1 | 5/2003 | Kuslich | |
| 2004/0010315 A1 | 1/2004 | Song | |
| 2004/0024463 A1 | 2/2004 | Thomas et al. | |
| 2005/0261769 A1 * | 11/2005 | Moskowitz | A61F 2/442 623/17.11 |
| 2006/0100706 A1 | 5/2006 | Shadduck | |
| 2006/0122701 A1 * | 6/2006 | Kiester | A61F 2/447 623/17.11 |
| 2006/0149385 A1 | 7/2006 | McKay | |
| 2006/0167547 A1 | 7/2006 | Suddaby | |
| 2006/0287729 A1 | 12/2006 | Segal et al. | |
| 2007/0118222 A1 | 5/2007 | Lang | |
| 2007/0173939 A1 | 7/2007 | Kim et al. | |
| 2007/0219634 A1 | 9/2007 | Greenhalgh | |
| 2007/0265627 A1 | 12/2007 | Dorchak | |
| 2008/0009876 A1 | 1/2008 | Sankaran et al. | |
| 2008/0021556 A1 | 1/2008 | Edie | |
| 2008/0021559 A1 | 1/2008 | Thramann | |
| 2008/0147193 A1 | 6/2008 | Matthis | |
| 2008/0188941 A1 * | 8/2008 | Grotz | A61F 2/4611 623/17.16 |
| 2008/0234687 A1 | 9/2008 | Schaller | |
| 2008/0281346 A1 | 11/2008 | Greenhalgh | |
| 2008/0281424 A1 | 11/2008 | Parry et al. | |
| 2009/0018524 A1 | 1/2009 | Greenhalgh | |
| 2009/0076607 A1 | 3/2009 | Aalsma et al. | |
| 2009/0138083 A1 | 5/2009 | Biyani | |
| 2009/0222043 A1 | 9/2009 | Altarac | |
| 2009/0222100 A1 | 9/2009 | Cipoletti et al. | |
| 2009/0234389 A1 | 9/2009 | Chuang | |
| 2010/0010633 A1 | 1/2010 | Kohm | |
| 2010/0198352 A1 | 8/2010 | Edie | |
| 2010/0217325 A1 | 8/2010 | Hochschuler | |
| 2010/0222884 A1 | 9/2010 | Greenhalgh | |
| 2010/0234956 A1 | 9/2010 | Attia | |
| 2010/0286783 A1 * | 11/2010 | Lechmann | A61F 2/3094 623/17.12 |
| 2010/0292796 A1 | 11/2010 | Greenhalgh | |
| 2011/0022090 A1 | 1/2011 | Gordon | |
| 2011/0029082 A1 | 2/2011 | Hall | |
| 2011/0035011 A1 | 2/2011 | Cain | |
| 2011/0046748 A1 | 2/2011 | Martin | |
| 2011/0093074 A1 | 4/2011 | Glerum | |
| 2011/0130835 A1 | 6/2011 | Ashley | |
| 2011/0172774 A1 | 7/2011 | Varela | |
| 2011/0190816 A1 | 8/2011 | Sheffer | |
| 2011/0282453 A1 | 11/2011 | Greenhalgh | |
| 2011/0301712 A1 * | 12/2011 | Palmatier | A61F 2/4455 623/17.16 |
| 2011/0319997 A1 | 12/2011 | Glerum | |
| 2012/0029636 A1 | 2/2012 | Ragab | |
| 2012/0035729 A1 | 2/2012 | Glerum et al. | |
| 2012/0046748 A1 | 2/2012 | Weiman | |
| 2012/0059470 A1 | 3/2012 | Weiman | |
| 2012/0083889 A1 | 4/2012 | Purcell | |
| 2012/0089185 A1 | 4/2012 | Gabelberger | |
| 2012/0109319 A1 | 5/2012 | Perisic | |
| 2012/0209386 A1 | 8/2012 | Triplett et al. | |
| 2012/0271396 A1 | 10/2012 | Zheng | |

(56) References Cited

U.S. PATENT DOCUMENTS

| | | |
|---|---|---|
| 2012/0277878 A1 | 11/2012 | Sommerich |
| 2012/0290090 A1 | 11/2012 | Glerum et al. |
| 2012/0303126 A1 | 11/2012 | Kirschman |
| 2013/0023996 A1 | 1/2013 | McCormack |
| 2013/0184822 A1 | 7/2013 | Kleiner |
| 2014/0031938 A1* | 1/2014 | Lechmann .............. A61F 2/442 623/17.16 |
| 2014/0039625 A1 | 2/2014 | To et al. |
| 2014/0172106 A1 | 6/2014 | To et al. |
| 2014/0243981 A1 | 8/2014 | Davenport et al. |
| 2015/0073555 A1 | 3/2015 | To et al. |
| 2015/0157464 A1 | 6/2015 | To et al. |
| 2016/0015530 A1 | 1/2016 | To et al. |
| 2016/0213483 A1 | 7/2016 | To et al. |

FOREIGN PATENT DOCUMENTS

| | | |
|---|---|---|
| EP | 1233732 | 2/2001 |
| EP | 2327377 | 3/2002 |
| EP | 1532949 | 11/2003 |
| EP | 2237748 | 1/2009 |
| JP | 2009/505686 | 7/2005 |
| WO | WO 1996/040015 | 6/1996 |
| WO | WO 2000/044319 | 1/2000 |
| WO | WO 2001/066047 | 7/2001 |
| WO | WO 2008/005627 | 5/2007 |
| WO | WO 2007/076374 | 7/2007 |
| WO | WO 2008/035849 | 7/2007 |
| WO | WO 2008/033457 | 3/2008 |
| WO | WO 2008/089252 | 7/2008 |
| WO | WO 2008/121162 | 10/2008 |
| WO | WO 2010/077359 | 7/2010 |
| WO | PCT/US2013/052799 | 7/2012 |
| WO | PCT/US2013/073435 | 12/2013 |
| WO | PCT/US2014/054437 | 2/2014 |
| WO | WO 2016/118608 | 1/2015 |

OTHER PUBLICATIONS

U.S. Appl. No. 61/875,688, To, filed Oct. 4, 2013
U.S. Appl. No. 14/701,013, To, filed Apr. 30, 2015.
Search report for PCT/US2013/052799, dated Dec. 2, 2012.
Written opinion and search report for PCT/US2013/073435, dated Apr. 30, 2012.
Written opinion and search report for PCT/US2014/054437, dated Jan. 6, 2015.
Basho, R. et al. Lateral interbody fusion: Indications and techniques. Operative techniques in orthopaedics 21(3): 204-207 (Sep. 2011).
Caliber. www.globusmedical.com [online] URL: http://www.globusmedical.com/mis/166-caliber [retrieved on Jul. 27, 2012].
Cole, D. et al. Comparison of low back fusion techniques: transforaminal lumbar interbody fusio (TLIF) or posterior lumbar interbody fusion (PLIF) approaches. Curr rev Musculoskelet med 2(2): 118-126 published online Apr. 29, 2009 Doi: 1007/s12178-009-9053-B10 [retrieved Jun. 2009].
CAPSTONE® PEEK spinal system PLIF anf TLIF surgical technique. Medtronic Sofamor Danek 1-36 (2009).
Coalign. Introducing AccuLIF expandable lumbar interbody fusion technology. [online] URL: http://www.coalign.com [retrieved on Jul. 27, 2012].
Chapman, C. A. Design of an expandable intervertebral cage utilizing shape memory alloys. University of Toledo and OhioLINK, 2011. [online] URL: http://etd.ohiolink.edu/view.cgi?acc_num=toledo1302226375 [retrieved Feb. 13, 2013].
Dorso-Lumbar Vertebral Body Cages DSC, Sintea Plustek. [online] URL: http://www.sinteaplustek.com/spine_dsc_eng.html [retrieved on Feb. 13, 2013].
Interbody Fusion Cage (Neo IC) Source, www.tradekorea.com [online] URL: http://www.tradekorea.com/product-detail/P00015150/Interbody_Fusion_Cage_Neo_IC_.html [retrieved Feb. 13, 2013].
Kaech, D.L. et al. Spinal restabilization procedures, diagnostic and therapeutic aspects of intervertebral fusion cages, artificial discs and mobile implants. Elsevier Science B.V. Part II: 121-204(2002).
Kiapour, A. et al. A biomechanical finite element study of subsidence and migration tendencies in stand-alone fusion procedures—comparison of an in situ expandable device with a rigid device. J Spine 1(4): 5 pages (2012).
Le Huec, J.C. et al. Endoscope surgery of the spine, a review of 4 years? Practice, maltrise orthopaedique. Jan. 1999 [online] URL: http://www.maitrise-orthop.com/viewPage_us.do?id=435 [retrieved on Feb. 5, 2013].
Powerbuilt. Powerbuilt 940378 medium tailpipe expander set. [online] URL: http://www.amazon.com/Powerbuilt-940377-Tailpipi-Expander-Series/dp/B004KED6A [retrieved on Feb. 17, 2013].
PR Newswire. Benvenue Medical starts enrolling patients in the post-market lift study on the luna interbody spacer system for degenerative disc disease. Mar. 20, 2012, [online] URL: http://www.prnewswire.com/news-releases/benvenue-medical-starts-enrolling-patients-in-the-post-market-lift-study-on-the-luna-interbody-spacer-system-for-degenerative-disc-disease-143441246.html [retrieved on Jan. 27, 2013].
Sasani, M. et al. Single-stage posterior corpectomy and expandable cage placement for treatment of thoracic or lumbar burst fractures. Spine 34(1): E33-E40 (Jan. 1, 2009).
Spineology. OptiMesh 1500E deploying grafting system. [online] URL: http://www.spineology.com/fb/intl/products/products/optimesh 1500e.html (retrieved Jun. 3, 2013).
Staxx XD, www.spinewave.com. [online] URL: http://www.spinewave.com/products/xd_us.html [retrieved on Jan. 27, 2013].
Synfix-LR System. Instruments and implants for stand-alone anterior lumbar interbody fusion (ALIF). Synthes SynFix-LR system technique guide 52 pages. (2010).
Transforaminal Lumbar Interbody Fusion (TLIF). Virgina spine institute, Reston Virgina. [online] URL: http://www.spinemd.com/operative-treatments/tlif-transforaminal-lumbat-interbody-fusion.com 1-6 (2013). [retrieved on Jun. 16, 2013].
Uchida, K. et al. Anterior expandable strut cage replacement for osteoporotic thoracolumbar vertebral collapse. J Neurosurg Spine 4(6): 454-462 (Jun. 2006).
Xenos. Cage mesh system for spine. Biotek Chetan Meditech Pvt. Ltd. [online] URL: http://www.biotekortho.net/spine-treatment.html [retrieved on Feb. 13, 2013].
Zeus-O, [online] URL: http://www.amendia.com/zeuso.html [retrieved on Jan. 27, 2013].
U.S. Appl. No. 15/194,463, To, filed Jan. 20, 2015.
Written opinion and search report for PCT/US2016/014100, dated Jan. 6, 2015.
U.S. Appl. No. 15/271,741, To, filed Sep. 21, 2016.

* cited by examiner

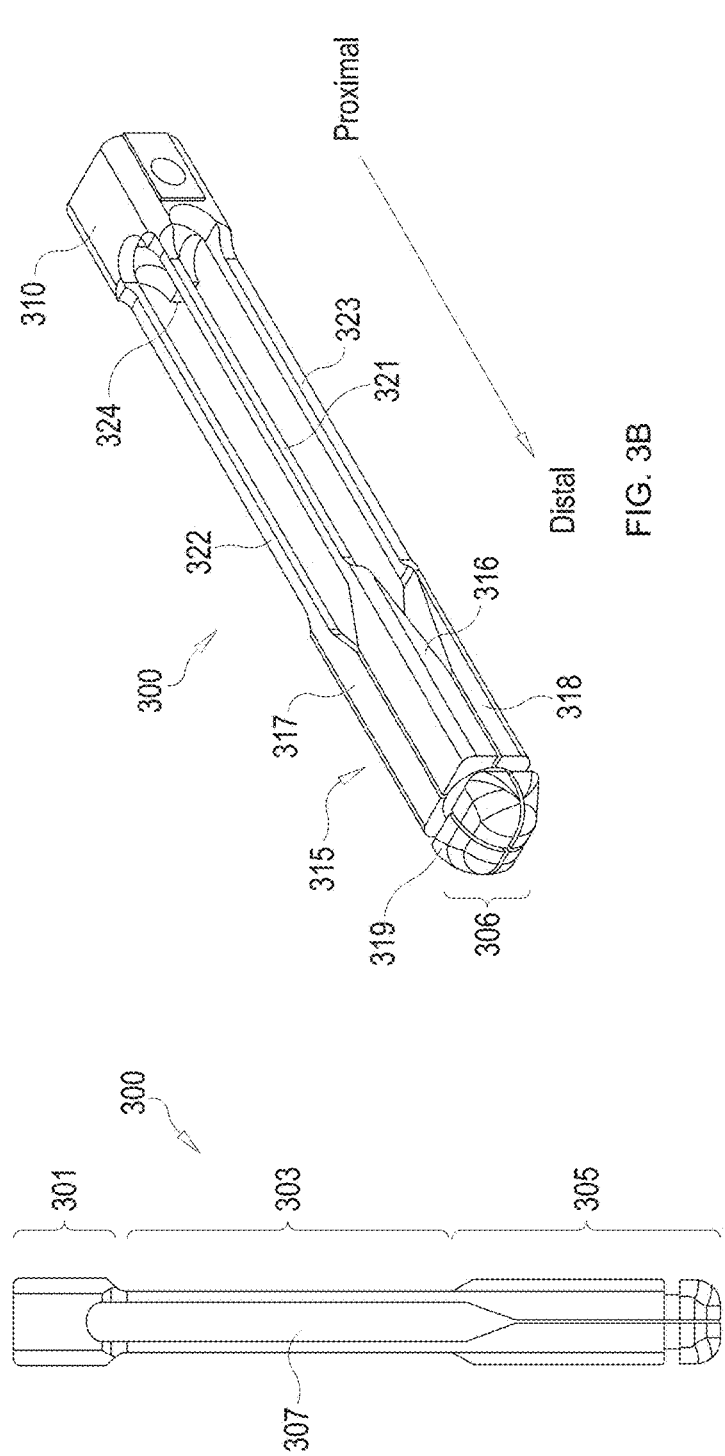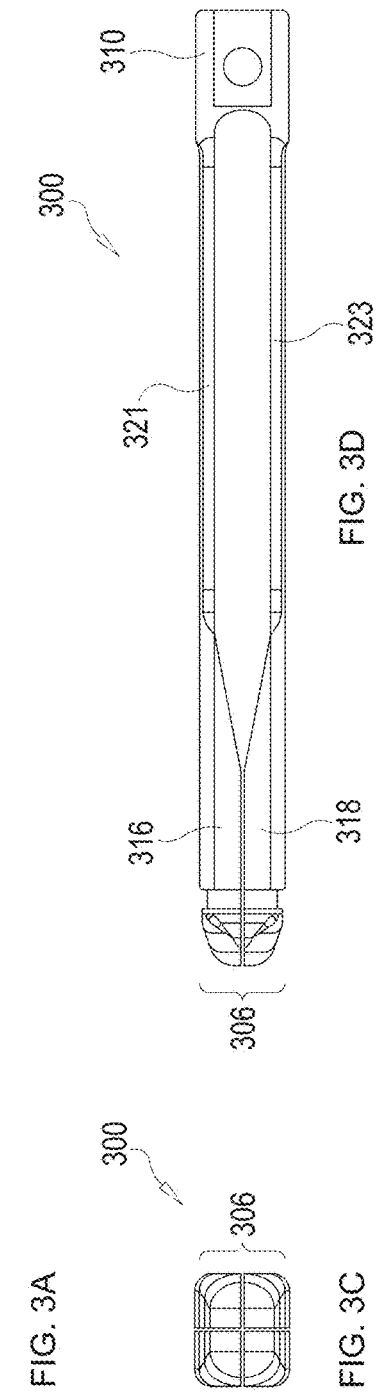

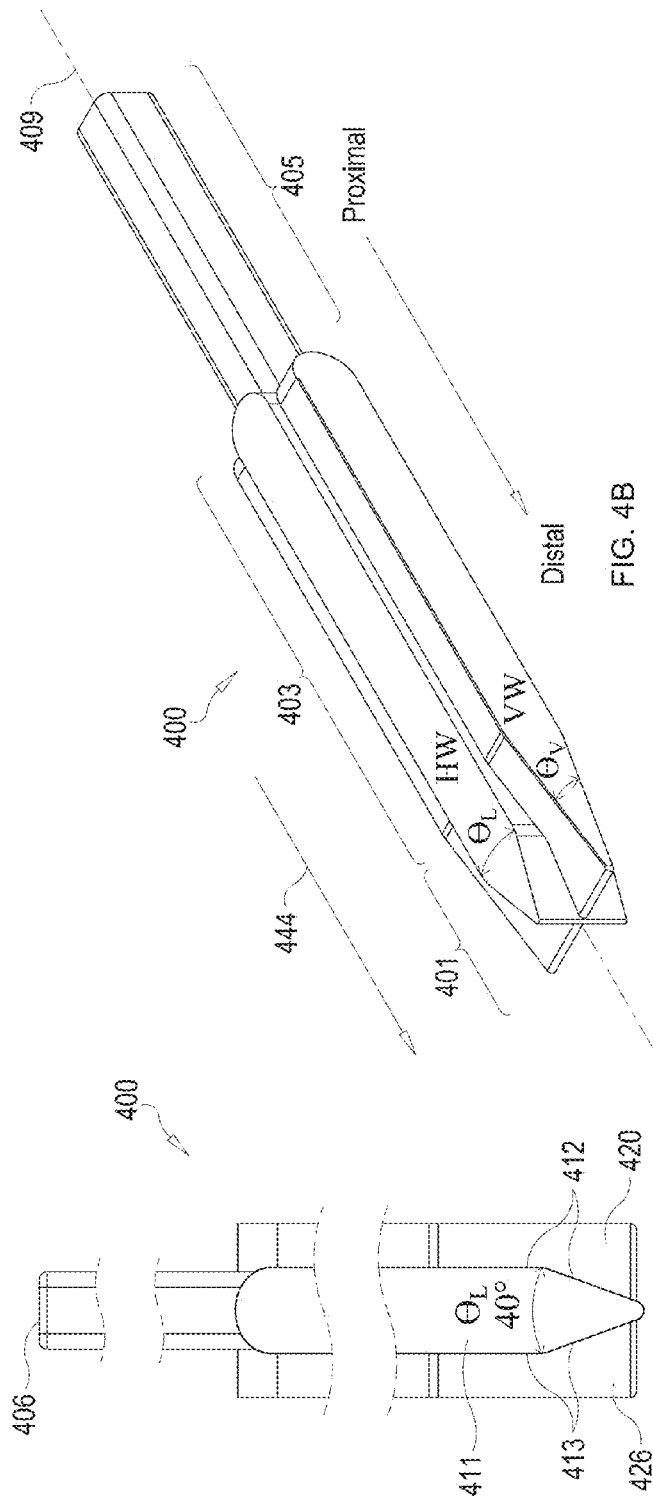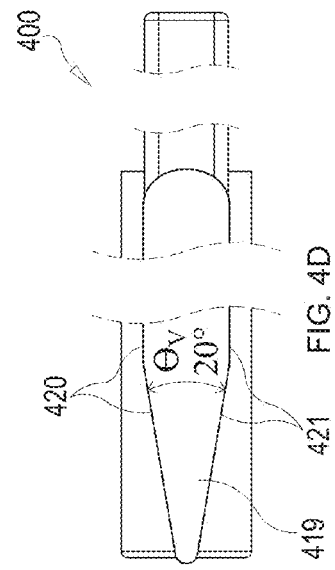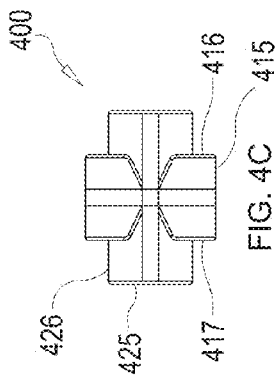

METHOD OF DISTRACTING AN INTERVERTEBRAL SPACE

CROSS-REFERENCE TO RELATED APPLICATIONS

This application is a continuation of U.S. application Ser. No. 14/480,416, filed Sep. 8, 2014, and claims the benefit of U.S. Application No. 61/875,688, filed Sep. 9, 2013, each of which is hereby incorporated herein by reference in its entirety.

BACKGROUND

Field of the Invention

The teachings herein are directed to systems and methods for distracting an intervertebral disc space using a staged, bilaterally expandable trial.

Description of the Related Art

Bone grafts are used in spinal fusion, for example, which is a technique used to stabilize the spinal bones, or vertebrae, and a goal is to create a solid bridge of bone between two or more vertebrae. The fusion process includes "arthrodesis", which can be thought of as the mending or welding together of two bones in a spinal joint space, much like a broken arm or leg healing in a cast. Spinal fusion may be recommended for a variety of conditions that might include, for example, a spondylolisthesis, a degenerative disc disease, a recurrent disc herniation, or perhaps to correct a prior surgery.

Bone graft material is introduced for fusion and a fusion cage can be inserted to help support the disc space during the fusion process. In fact, fusion cages are frequently used in such procedures to support and stabilize the disc space until bone graft unites the bone of the opposing vertebral endplates in the disc space. A transforaminal lumbar interbody fusion (TLIF), for example, involves placement of posterior instrumentation (screws and rods) into the spine, and the fusion cage loaded with bone graft can be inserted into the disc space. Bone graft material can be pre-packed in the disc space or packed after the cage is inserted. TLIF can be used to facilitate stability in the front and back parts of the lumbar spine promoting interbody fusion in the anterior portion of the spine. Fusion in this region can be beneficial, because the anterior interbody space includes an increased area for bone to heal, as well as to handle increased forces that are distributed through this area.

Unfortunately, therein lies a problem solved by the teachings provided herein. Currently available systems can be problematic in that the methods of introducing the fusion cage and bone graft material creates "subsidence" of the cage into the adjoining vertebrae, resulting in a narrowing of the formerly distracted disc space. This is because the cage is inserted near the middle of the endplate area which is softer than the areas at or near the peripheral zone of the endplate, and when it distracts, the cage actually sinks into the endplate creating the subsidence problem. The problem remains with state-of-the-art distraction instruments, such as the Medtronic SCISSOR JACK, paddle trials, or oversized trial shims (metallic wedges). Each of these state-of-the-art procedures introduce the distraction means narrowly (no wider than width of annulotomy) and then distract the intervertebral space with a narrow foot print that ranges from about 8 mm to about 11 mm wide.

Accordingly, and for at least the above reasons, those of skill in the art will appreciate distraction systems that facilitate an improved placement of distraction stresses across the verterbral endplates that define the distracted intervertebral space. Such systems are provided herein, the systems configured to (i) effectively and selectively place the distraction stresses in areas that include areas at or near the peripheral zones of the vertebral endplates to reduce the incidence of subsidence; (ii) reduce or eliminate the problem of failures resulting from subsidence; (iii) have a small maximum dimension of the trial in a collapsed state for a low-profile insertion into the annulus in a minimally-invasive manner, whether using only a unilateral approach or a bilateral approach; (iv) laterally expand within the intervertebral space to facilitate the effective and selective distribution of distraction stresses on the vertebral endplates; (v) vertically expand for distraction of the intervertebral space; (vi) provide an expansion in the intervertebral space without contracting the system in length to maintain a large footprint during the distraction process, distributing load over a larger area, including areas at or near the peripheral zones of the vertebral endplates; and, (vii) serve as a measuring device for the size of the intevebral space to facilitate selection of the size of the cage.

SUMMARY

The teachings herein are directed to systems and methods for distracting an intervertebral disc space using a staged, bilaterally expandable trial. Generally, the teachings are directed to a method of distracting an intervertebral space in a manner that addresses the problem of subsidence. The teachings include obtaining a bilaterally expandable trial that is configured to first expand laterally and then expand vertically to distract an intervertebral space having a top vertebral plate and a bottom vertebral plate. The trial is then inserted into the intervertebral space in a collapsed state. Once inserted, the trial then used for distracting the intervertebral space using a staged, bilateral expansion, the distracting including a first stage and a second stage. The first stage includes expanding the trial laterally toward the peripheral zones of the top vertebral plate and the bottom vertebral plate, and the second stage includes expanding the trial vertically to distract the intervertebral space.

As such, a staged, bilaterally-expandable trial for an intervertebral space is provided. In some embodiments, the trial comprises a bilaterally-expandable shell having a proximal region with an end, a mid-region, a distal region with an end, and a lumen. The proximal region can have a slider-guide, and the distal region can have a bilaterally-expandable head with 4 subheads that include a first top beam, a second top beam, a first bottom beam, and a second bottom beam. The mid-region can have 4 flex rods that include a first top flex rod, a second top flex rod, a first bottom flex rod, and a second bottom flex rod, each of which operably attaches the slider-guide to it's respective subhead.

One or more beam stabilizers can be included stabilize and/or align the subheads during operation of the device. A beam stabilizer, for example, can slidably translate, such that it is telescopic with respect to one or both subheads between which it is operably attached to stabilize and/or align the relationship between the subheads during operation of the device. In some embodiments, the beams can be stabilized with translatable, telescopic linear guides, such that the linear guide can telescope within itself. For example, the first top beam can be operably connected to the second top beam with a top telescopic beam stabilizer, the first top beam can be operably connected to the second top beam with a top telescopic beam stabilizer, the first top beam can be operably connected to the first bottom beam with a first side telescopic beam stabilizer, the second top beam can be operably connected to the second bottom beam with a second side telescopic beam stabilizer, and the first bottom beam can be operably connected to the second bottom beam with a bottom telescopic beam stabilizer. The beam stabilizer, or at least a portion thereof, can be fixably attached, or monolithically integral to, one or both beams between which it is operably connected or positioned in either a fixed or translatable configuration in the trial.

The trial can be expanded first laterally, and then vertically, using any means known to one of skill. For example, the trial can also comprise a shim having a proximal region with an end; a mid-region; a distal region with an end; a central axis; a top surface with a first top-lateral surface and a second top-lateral surface; a bottom surface with a first bottom-lateral surface and a second bottom-lateral surface; a first side surface with a first top-side surface and a first bottom-side surface; and, a second side surface with a second top-side surface and a second bottom-side surface. The shim can be configured for a proximal-to-distal axial translation in the lumen of the shell that induces a lateral force on the 4 subheads followed by a vertical force on the 4 subheads for a staged, bilateral expansion in vivo that includes a lateral expansion of the head followed by a vertical expansion of the head in an intervertebral space having a top vertebral endplate, a bottom vertebral endplate, and an annulus.

The head of the trial can be configured with a proximal portion having an end; a distal portion having an end; and, a central shell axis of the expanded state; the head adapted for slidably-engaging with the shim in vivo following placement of the trial in the intervertebral space through the annular opening, the slidably-engaging including axially-translating the shim in the lumen of the shell from the proximal end of the lumen toward the distal end of the lumen in vivo; the translating including keeping the central shim axis at least substantially coincident with the central shell axis during the translating.

The teachings are also directed to systems that include means for applying an axial proximal-to-distal force on a shim that expands the trial. In some embodiments, the proximal end of the shim can be configured to receive the axial proximal-to-distal force through an actuation bar for the axial translation, the actuation bar having a proximal portion with a proximal end, a distal portion with a distal end, and configured to transfer the axial proximal-to-distal force to the shim through the slider-guide.

The systems can include an actuation means operably attached to the proximal end of the actuation bar to transfer the axial proximal-to-distal force to the shim through the distal end of the actuation bar. In some embodiments, the actuation bar receives the axial proximal-to-distal force from an actuation screw that can be operably attached to the proximal end of the actuation bar to transfer the force to the shim through the distal end of the actuation bar. The systems can further comprise a retractable retention plunger configured for retaining the trial in the collapsed state and releasing the trial for expansion into the expanded state.

The head of the trial can have a collapsed dimension that facilitates insertion to the intervertebral space and an expanded dimension that facilitates the desired lateral expansion and vertical expansion in the intervertebral space. In some embodiments, the head of the trial can have a collapsed state with a transverse cross-section having a maximum dimension ranging from 5 mm to 18 mm for placing the frame in an intervertebral space through an annular opening for expansion in the intervertebral space. And, in some embodiments, the head of the trial can have an expanded state with a transverse cross-section having a maximum dimension ranging from 6.5 mm to 28 mm, 7.5 mm to 28 mm, 8.5 mm to 28 mm, 6.5 mm to 27 mm, 6.5 mm to 25 mm, 6.5 mm to 23 mm, 6.5 mm to 21 mm, 6.5 mm to 19 mm, 6.5 mm to 18 mm, or any range therein in increments of 1 mm, in the intervertebral space. In some embodiments, the shim can have a transverse cross-section with a maximum dimension ranging from 5 mm to 18 mm, 6 mm to 18 mm, 7 mm to 18 mm, 5 mm to 15 mm, 5 mm to 16 mm, 5 mm to 17 mm, or any range therein in increments of 1 mm, for translating the shim in the lumen of the shell.

In some embodiments, the shim can have a horizontal wedge configured to laterally-expand the trial, and a vertical wedge configured to vertically-expand the trial. In some embodiments, the shim can have a top wedge configured to laterally-expand the first top beam away from the second top beam, a bottom wedge configured to laterally-expand the first bottom beam away from the second bottom beam, a first side wedge configured to vertically-expand the first top beam away from the first bottom beam, and a second side wedge configured to vertically-expand the second top beam away from the second bottom beam. In some embodiments, the proximal portion of the first top beam and the proximal portion of the second top beam can be configured to complement the top wedge at the onset of the lateral expansion during the proximal-to-distal axial translation; and, the proximal portion of the first bottom beam and the proximal portion of the second bottom beam can be configured to complement the bottom wedge at the onset of the lateral expansion during the proximal-to-distal axial translation. In some embodiments, the distance, $D_{STAGING}$, between the onset of the lateral expansion and the onset of the vertical translation can range from 2 mm to 10 mm.

In some embodiments, the proximal portion of the first top beam and the proximal portion of the first bottom beam can be configured to complement the first side wedge during the proximal-to-distal axial translation for the vertical expansion; and, the proximal portion of the second top beam and the proximal portion of the second bottom beam can be configured to complement the second side wedge during the proximal-to-distal axial translation for the vertical expansion.

In some embodiments, the first top beam can include a proximal portion having an end, a distal portion having an end, and a central axis; the first top beam configured for contacting a first top chamfer of the shim in the expanded state, the central axis of the first top beam at least substantially on (i) a top plane containing the central axis of the first top beam and the central axis of a second top beam and (ii) a first side plane containing the central axis of the first top beam and the central axis of a first bottom beam. Likewise, the second top beam can include a proximal portion having an end, a distal portion having an end, and a central axis; the second top beam configured for contacting a second top chamfer of the shim in the expanded state, the central axis of the second top beam at least substantially on (i) the top plane and (ii) a second side plane containing the central axis of the second top beam and the central axis of a second bottom beam. Likewise, the first bottom beam can include a proximal portion having an end, a distal portion having an end, and a central axis; the first bottom beam configured for contacting a first bottom chamfer of the shim in the expanded state, the central axis of the first bottom beam at least substantially on (i) a bottom plane containing the central axis of the first bottom beam and the central axis of a second top beam and (ii) the first side plane. Moreover, the second bottom beam can include a proximal portion having an end, a distal portion having an end, and a central axis; the second bottom beam configured for contacting a second bottom chamfer of the shim in the expanded state, the central axis of the second bottom beam being at least substantially on (i) the bottom plane and (ii) a second side plane containing the central axis of the second bottom beam and the second top beam.

In some embodiments, the first top beam can include a proximal portion having an end, a distal portion having an end, and a central axis; the first top beam configured for contacting a first top-lateral surface of the shim and a first top-side surface of the shim in the expanded state, the central axis of the first top beam at least substantially on (i) a top plane containing the central axis of the first top beam and the central axis of a second top beam and (ii) a first side plane containing the central axis of the first top beam and the central axis of a first bottom beam. Likewise, the second top beam can include a proximal portion having an end, a distal portion having an end, and a central axis; the second top beam configured for contacting the second top-lateral surface of the shim and the second top-side surface of the shim in the expanded state, the central axis of the second top beam at least substantially on (i) the top plane and (ii) a second side plane containing the central axis of the second top beam and the central axis of a second bottom beam. Likewise, the first bottom beam can include a proximal portion having an end, a distal portion having an end, and a central axis; the first bottom beam configured for contacting the first bottom-lateral surface of the shim and the first bottom-side surface of the shim in the expanded state, the central axis of the first bottom beam at least substantially on (i) a bottom plane containing the central axis of the first bottom beam and the central axis of a second top beam and (ii) the first side plane. Moreover, the second bottom beam can include a proximal portion having an end, a distal portion having an end, and a central axis; the second bottom beam configured for contacting the second bottom-lateral surface of the shim and the second bottom-side surface of the shim in the expanded state, the central axis of the second bottom beam being at least substantially on (i) the bottom plane and (ii) a second side plane containing the central axis of the second bottom beam and the second top beam.

In some embodiments, the shim can comprise a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

In some embodiments, the shim can comprise a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

The shell can be formed using any method of construction known to one of skill, for example, multi-component or single unit. In some embodiments, the shell can be a single-unit formed from a single body of material, and the slider-guide, head, and flex rods can be monolithically integral.

Accordingly, the teachings include a method of distracting an intervertebral space using the trials taught herein. In some embodiments, the method can comprise creating a point of entry into an intervertebral disc, the intervertebral disc having a nucleus pulposus surrounded by an annulus fibrosis, and the point of entry having the maximum lateral dimension created through the annulus fibrosis. The methods can include removing the nucleus pulposus from within the intervertebral disc through the point of entry, leaving the intervertebral space for expansion of the head of the trial within the annulus fibrosis, the intervertebral space having the top vertebral plate and the bottom vertebral plate. The methods can include inserting the head in the collapsed state through the point of entry into the intervertebral space; and, distracting the intervertebral space using a staged, bilateral expansion that includes a first stage and a second stage. The distracting can include a first stage and a second stage, the first stage including expanding the head laterally toward the peripheral zones of the top vertebral plate and the bottom vertebral plate; and, the second stage including expanding the head vertically to distract the intervertebral space, the pressure for the expansion occurring preferably, and at least primarily, at or near the peripheral zones of the top vertebral plate and the bottom vertebral plate. In some embodiments, the lateral dimension of the point of entry ranges from about 5 mm to 18 mm, 6 mm to 18 mm, 7 mm to 18 mm, 5 mm to 15 mm, 5 mm to 16 mm, 5 mm to 17 mm, or any range therein in increments of 1 mm.

In some embodiments, the distracting includes selecting an amount of lateral expansion independent of an amount of vertical expansion. And, in some embodiments, the distracting includes measuring the amount of lateral expansion independent of the amount of vertical expansion.

In some embodiments, the distracting includes as a first stage of lateral expansion, inserting a top wedge into the head between the first top beam and the second top beam, the top wedge composing a portion of the shim and configured to laterally-expand the first top beam away from the second top beam; and, inserting a bottom wedge into the head between the first bottom beam and the second bottom beam, the bottom wedge configured to laterally-expand the first bottom beam away from the second bottom beam. And, as a second stage of expansion, inserting a first side wedge into the head between the first top beam and the first bottom beam, the first side wedge configured to laterally-expand the first top beam away from the first bottom beam; and, inserting a second side wedge into the head between the second top beam and the second bottom beam, the second side wedge configured to laterally-expand the second top beam away from the second bottom beam.

In some embodiments, the distracting includes selecting a shim having a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

In some embodiments, the distracting includes selecting a shim having a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

BRIEF DESCRIPTION OF THE FIGURES

FIGS. 3A-3D illustrate a staged, bilaterally-expandable trial, according to some embodiments.

FIGS. 4A-4D illustrate a shim for the staged, bilaterally expanding trial, according to some embodiments.

DETAILED DESCRIPTION OF THE INVENTION

Systems and methods for distracting an intervertebral disc space using a staged, bilaterally expandable trial are provided. Generally speaking, a system for distracting an intervertebral disc space using a staged, bilaterally expandable trial is provided. Generally, the teachings are directed to a method of distracting an intervertebral space in a manner that addresses the problem of subsidence by selectively applying distraction forces to stronger portions of the vertebral endplates of the intervertebral space. It should be appreciated that the term "trial" can be used interchangeably with the term "distractor" in many embodiments.

Figure 1A:
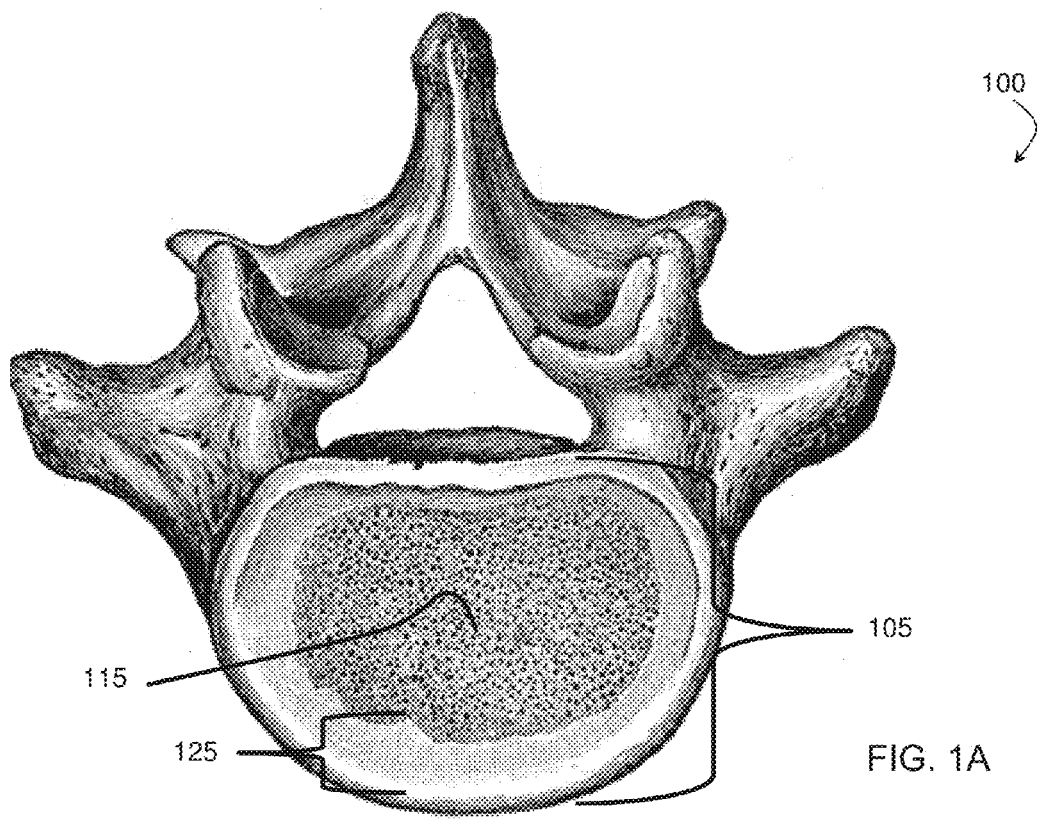
FIGS. 1A and 1B illustrate a sketch of an endplate of a vertebral body and a representative photograph of an intervertebral space using a cadaver intervertebral body and disc, according to some embodiments.
Figure 1B:
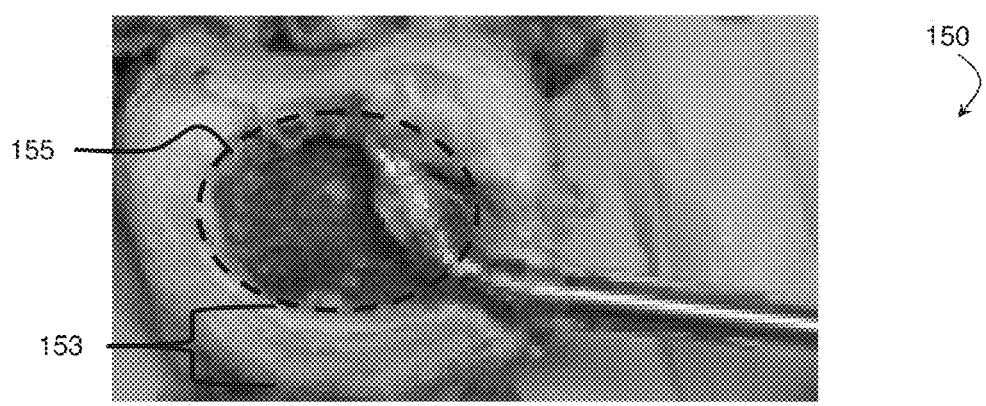

FIGS. 1A and 1B illustrate a sketch of an endplate of a vertebral body and a representative photograph of an intervertebral space using a cadaver intervertebral body and disc, according to some embodiments. This illustration provides a reference to discuss the state-of-the-art methods of introducing the fusion cage and bone graft material which create "subsidence" of the cage into the adjoining vertebrae, resulting in a narrowing of the formerly distracted disc space. As shown in FIG. 1A, the vertebral body 100 has an endplate 105 with a mid-region 115 and a peripheral zone 125. The problem occurs because the cage is typically inserted at or near the mid-region 115 which is softer than the areas at or near the peripheral zone 125 of the endplate 105, and when it distracts, the cage actually sinks into the endplate 105 creating the subsidence problem. The problem remains with state-of-the-art distraction instruments, such as the Medtronic SCISSOR JACK, paddle trials, or oversized trial shims (metallic wedges). Each of these state-of-the-art procedures introduce the distraction means narrowly (no wider than width of annulotomy) and then distract the intervertebral space with a narrow foot print that ranges, for example, from about 8 mm to about 11 mm wide. FIG. 1B illustrates a cadaver intervertebral body 150, and the annulus 153 that surrounds the intervertebral space 155 that receives the trial.

In some embodiments, the phrase "at or near the peripheral zone" of a vertebral endplate can be interpreted as meaning "at least substantially away from the central portion of the area of the vertebral endplate. A distraction pressure can be applied, for example, at least substantially away from the central portion where greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or more of the surface area of a pair of subheads that is facing, or in some embodiments in contact or potential contact with, their respective endplate outside of the central portion. In some embodiments, the "central portion" can be defined as a scaled-down area on the surface of the endplate, and thus sharing a plane with the surface of the endplate, sharing a center-point on the plane, and sharing the same general shape as the total area of the endplate, albeit scaled-down. As such, an overlay of the central portion that is placed on the total area with the same orientation, and placed carefully such that the center-point of the central portion is shared/concentric with the center-point of the total area, leaves a "remaining area" or "remainder" around the periphery of the total area that can be defined, for example, as either a "peripheral zone" in some embodiments, or "at-or-near the peripheral zone," in some embodiments. The following table shows a hypothetical relationship between the radius and the area of a hypothetical endplate model using for simplicity a circular area having a diameter of 25 mm.

| scale (fraction of total area) | diameter (mm) | radius (mm) | area (mm)^2 | |
|---|---|---|---|---|
| 1.00 | 25.00 | 12.50 | 490.88 | total area |
| 0.70 | | 10.46 | 343.62 | Scaled |
| 0.60 | | 9.68 | 294.53 | Scaled |
| 0.50 | | 8.84 | 245.44 | Scaled |
| 0.40 | | 7.91 | 196.35 | Scaled |
| 0.30 | | 6.85 | 147.26 | Scaled |
| 0.20 | | 5.59 | 98.18 | Scaled |
| 0.10 | | 3.95 | 49.09 | Scaled |

Interestingly, a central portion of the hypothetical circular area having area based on a radius of 6.85 mm, which is about 55% of the total radius provides only 30% of the total area. As such, if the central portion amounts to only about 50% of the total area, it uses about two-thirds of the radius of the total area, leaving a radial dimension for the peripheral zone that is about 3.66 mm wide for the hypothetical endplate having the diameter of 25 mm. In some embodiments, the central portion can be 10%, 15%, 20%, 25%, 30%, 35%, 40%, 45%, 50%, 55%, 60%, 65%, 70%, or any percentage therein increments of 1%, of the total area. In some embodiments, the peripheral zone can have a radial dimension, or radial width, that is 2 mm, 3 mm, 4 mm, 5 mm, 6 mm, 7 mm, 8 mm, or any 0.1 mm increment therein. It should be appreciated that the radial dimension, or radial width, is the thickness of the peripheral zone area that circumscribes the periphery of the endplate as shown in FIG. 1, 125, and further described above qualitatively with respect to the remainder of the overlay of the central portion on the total area. One of skill will appreciate that a peripheral zone does not have to be uniform, and that the teachings provided herein to define the peripheral zone, or the area at-or-near the peripheral zone, are taught to further clarify boundaries of some embodiments by distinguishing both a configuration and function of the trials and systems taught herein from the current state-of-the-art. As such, it should be appreciated that the trials can be further configured to have a contour, whether laterally, vertically, or both laterally and vertically, that is at least substantially complementary to the areas within the peripheral zone, or at-or-near the peripheral zone, during operation of the trials provided herein. For example, the trial can have a linear, curved, or curvalinear lateral surface; a flat or convex vertical surface; or, some combination thereof, upon expansion to provide a shape that is at least substantially complementary to the peripheral zone of the endplates upon expansion.

Figure 2:
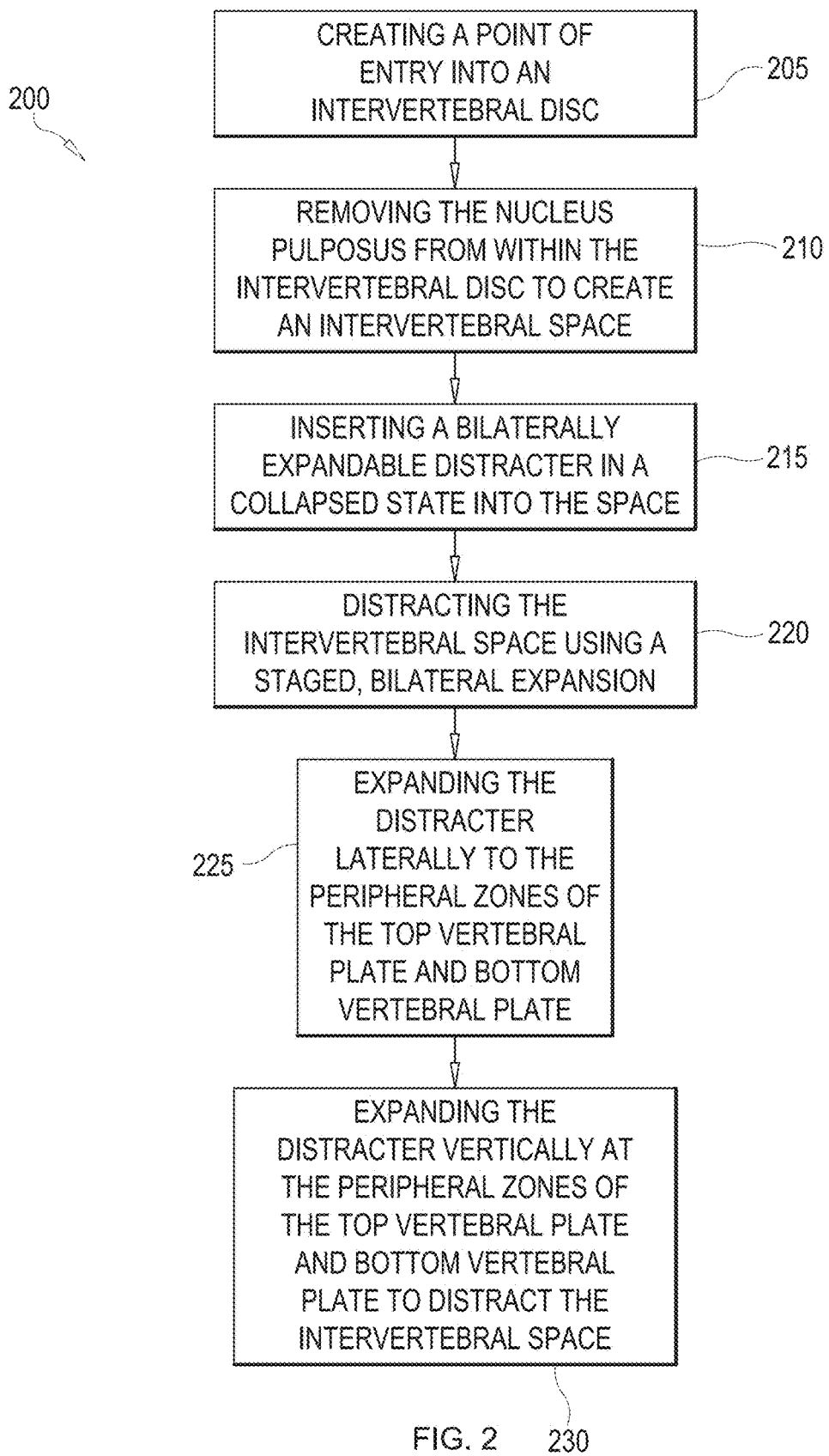
FIG. 2 illustrates a process of using a staged, bilaterally-expandable trial for distracting an intervertebral space, according to some embodiments.

FIG. 2 illustrates a process of using a staged, bilaterally-expandable trial for distracting an intervertebral space, according to some embodiments. The method 200 of distracting an intervertebral space can include, for example, obtaining a bilaterally expandable trial that is configured to first expand laterally and then expand vertically to distract an intervertebral space having a top vertebral plate and a bottom vertebral plate. The method 200 includes creating 205 a point of entry into an intervertebral disc and removing 210 the nucleus pulposus from within the intervertebral disc to create an intervertebral space. The method further includes inserting 215 the trial into the intervertebral space in a collapsed state. Once inserted, the trial then used for distracting 220 the intervertebral space using a staged, bilateral expansion, the distracting including a first stage and a second stage. The first stage includes laterally expanding 225 the trial to a position at or near the peripheral zones of the top vertebral plate and the bottom vertebral plate, and the second stage includes vertically expanding 230 the trial at or near the peripheral zones of the top vertebral plate and the bottom vertebral plate to distract the intervertebral space while avoid the problem of subsidence.

FIGS. 3A-3D illustrate a staged, bilaterally-expandable trial, according to some embodiments. As shown in FIG. 3A, a top view of the trial 300, the trial 300 comprises a bilaterally-expandable shell having a proximal region 301 with an end 302, a mid-region 303, a distal region 305 with an end 306, and a lumen 307. As shown in FIG. 3B, the proximal region 301 can have a slider-guide 310, and the distal region 305 can have a bilaterally-expandable head 315 with 4 subheads 316,317,318,319 that include a first top beam 316, a second top beam 317, a first bottom beam 318, and a second bottom beam 319. The mid-region can have 4 flex rods 321,322,323,324 that include a first top flex rod 321, a second top flex rod 322, a first bottom flex rod 323, and a second bottom flex rod 324, each of which operably attaches the slider-guide 310 to it's respective subhead. As shown in FIG. 3C, the end 306 of the distal region can be tapered or otherwise round, configured in the collapsed state in some embodiments, for example, as a bullet-nosed tip to avoid damage to the inner annulus during the distraction procedure. As shown in FIG. 3D, a side view of the trial 300, and comparing to FIG. 3A, the ratio of $\theta_V$ to $\theta_L$ is 1:2 in this embodiment for a staged bilateral expansion of the trial. The example dimensions shown in FIGS. 3A-3D are in inches.

In some embodiments, the rods can range from 2 cm to 4 cm in length and 0.5 mm to 2 mm in thickness. In some embodiments, the rods can be 1 mm wide by 1 mm thick and have a length of 2.5 cm.

In some embodiments, the shell can be wider at the head than the region proximal to the head. In some embodiments, the shell can be taller at the head than the region proximal to the head.

The trial can be expanded first laterally, and then vertically, using any means known to one of skill. FIGS. 4A-4D illustrate a shim for the staged, bilaterally expanding trial, according to some embodiments. As shown in FIGS. 4A and 4B, the trial can also comprise a shim 400 having a proximal region 401 with an end 402; a mid-region 403; a distal region 405 with an end 406; a central axis 409; a top surface 411 with a first top-lateral surface 412 and a second top-lateral surface 413; a bottom surface 415 with a first bottom-lateral surface 416 and a second bottom-lateral surface 417; a first side surface 419 with a first top-side surface 420 and a first bottom-side surface 421; and, a second side surface 425 with a second top-side surface 426 and a second bottom-side surface 427. The shim can be configured for a proximal-to-distal axial translation 444 in the lumen of the shell that induces a lateral force on the 4 subheads followed by a vertical force on the 4 subheads for a staged, bilateral expansion in vivo that includes a lateral expansion of the head followed by a vertical expansion of the head in an intervertebral space having a top vertebral endplate, a bottom vertebral endplate, and an annulus.

The head of the trial can be configured with a proximal portion having an end; a distal portion having an end; and, a central shell axis of the expanded state; the head adapted for slidably-engaging with the shim in vivo following placement of the trial in the intervertebral space through the annular opening, the slidably-engaging including axially-translating the shim in the lumen of the shell from the proximal end of the lumen toward the distal end of the lumen in vivo; the translating including keeping the central shim axis at least substantially coincident with the central shell axis during the translating.

In some embodiments, the shim has a cross-shaped cross-section which is formed by the crossing of a vertical wedge and a lateral wedge. Both wedges can taper down to an edge at the distal end. When the shim slides distally relative to the shell, it can push against the inner chamfers on the subheads to move the subheads away from each other to expand the shell head. When the head expands, the subheads are pushed outward and flex the respective rods outward. When the shim is pulled back, the head collapses because the rods flex back in. Additionally, a coil spring can be wrapped around an outer transverse groove on the head to further help to pull the subheads together when the shim is pulled back. An elastic band (silicone) can be used rather than coil spring. The shell-shim assembly can be designed such that the lateral expansion wedge engages with the chamfers on the subheads before the vertical expansion wedge engages so that the head expands laterally before it expands vertically. In some embodiments, this can be achieved by having the lateral expansion chamfers (angled relative to vertical plane along long axis of device) angled more from the long axis than the vertical expansion chamfers. In one embodiment, the lateral expansion chamfers are 20 degrees from long axis and the vertical expansion chamfers are 10 degrees from the axis. In one embodiment, the bevels on the wedges are parallel to the chamfers on the subheads. In some embodiments, the bevels on the lateral expansion wedge can be advanced beyond the lateral expansion chamfers before the vertical expansion wedge engages the vertical expansion chamfers on the subheads. Once the bevels on the lateral expansion wedge is advanced beyond the chamfer, there is no more head expansion as the shim is advanced further distally. As such, the shim can continue to be advanced distally to expand the head vertically without further lateral expansion.

In some embodiments, the subheads can be 4.5 mm thick laterally and the lateral expansion wedge tapers up to 4 mm wide to allow for lateral expansion from 9 mm to 13 mm. The collapsed thickness of the head in any direction can be the sum of the thicknesses of the subheads in that direction, and the maximum amount of expansion can be the maximum thickness of the wedge. In some embodiments, the subheads can be 3.35 mm in the vertical direction and the vertical expansion wedges can be 4.3 mm tall to allow for vertical expansion from 6.7 mm to 11 mm. In some embodiments, the subheads can be 4 mm tall in the vertical direction and the vertical expansion wedges can be 6 mm tall to allow for vertical expansion from 8 mm to 14 mm.

In some embodiments, the shim can have a tail that extends 2 cm to 4 cm long proximal from the wedge part and a rectangular cross section that is 2 mm to 5 mm thick. The tail can be configured to slide along a rectangular hole in the slider guide. This construct can be adapted to limit the movement of the wedges to the long axis direction. In some embodiments, the shell rods can be flush with a groove formed by an intersection between the vertical and lateral wedges to help keep the assembly stable for insertion into the disc. In some embodiments, the vertical wedges can be flush with the vertical chamfers on the subheads in the collapsed state to further stabilize the subheads from movement in the lateral direction for insertion into the disc space.

One of skill will also appreciate having a method of designing the shape of the head upon expansion. In some embodiments, for example, it may be beneficial for the distal expansion of the head to be larger than the proximal expansion of the head to account for a lordosis in the subject. Or, in some embodiments, for example, it may be considered beneficial for the expanded head to have a convexity in the subheads that applies a pressure to either endplate. As such, in some embodiments, the expanding includes selecting a shim configured to vertically expand the distal end of the cage more than the proximal end of the cage. Or, in some embodiments, the expanding includes selecting a shim configured to create a convex surface on the top surface of the top wall, for example, to at least substantially complement the concavity of the respective top vertebral plate, and/or the bottom surface of the bottom wall to at least substantially complement the concavity of the respective bottom vertebral plate. Or, in some embodiments, the expanding includes selecting a shim configured to laterally expand the distal end of the cage more than the proximal end of the cage.

One of skill will appreciate that the trial or the shim can be fabricated using any desirable material having the requisite material characteristics of strength, flexibility, biocompatibility, and the like. In some embodiments, the shell and the shim can be fabricated from stainless steel but can be made of any metal or hard plastics such as ULTEM and PEEK.

The head of the trial can have a collapsed dimension that facilitates insertion to the intervertebral space and an expanded dimension that facilitates the desired lateral expansion and vertical expansion in the intervertebral space. In some embodiments, the head of the trial can have a collapsed state with a transverse cross-section having a maximum dimension ranging from 5 mm to 18 mm, 6 mm to 18 mm, 7 mm to 18 mm, 5 mm to 15 mm, 5 mm to 16 mm, 5 mm to 17 mm, or any range therein in increments of 1 mm, for placing the frame in an intervertebral space through an annular opening for expansion in the intervertebral space. And, in some embodiments, the head of the trial can have an expanded state with a transverse cross-section having a maximum dimension ranging from 6.5 mm to 28 mm, 7.5 mm to 28 mm, 8.5 mm to 28 mm, 6.5 mm to 27 mm, 6.5 mm to 25 mm, 6.5 mm to 23 mm, 6.5 mm to 21 mm, 6.5 mm to 19 mm, 6.5 mm to 18 mm, or any range therein in increments of 1 mm, in the intervertebral space. In some embodiments, the shim can have a transverse cross-section with a maximum dimension ranging from 5 mm to 18 mm for translating the shim in the lumen of the shell.

In some embodiments, the shim can have a horizontal wedge, HW, configured to laterally-expand the trial, and a vertical wedge, VW, configured to vertically-expand the trial. In some embodiments, the shim can have a top wedge configured to laterally-expand the first top beam away from the second top beam, a bottom wedge configured to laterally-expand the first bottom beam away from the second bottom beam, a first side wedge configured to vertically-expand the first top beam away from the first bottom beam, and a second side wedge configured to vertically-expand the second top beam away from the second bottom beam. In some embodiments, the proximal portion of the first top beam and the proximal portion of the second top beam can be configured to complement the top wedge at the onset of the lateral expansion during the proximal-to-distal axial translation; and, the proximal portion of the first bottom beam and the proximal portion of the second bottom beam can be configured to complement the bottom wedge at the onset of the lateral expansion during the proximal-to-distal axial translation.

Figure 5:
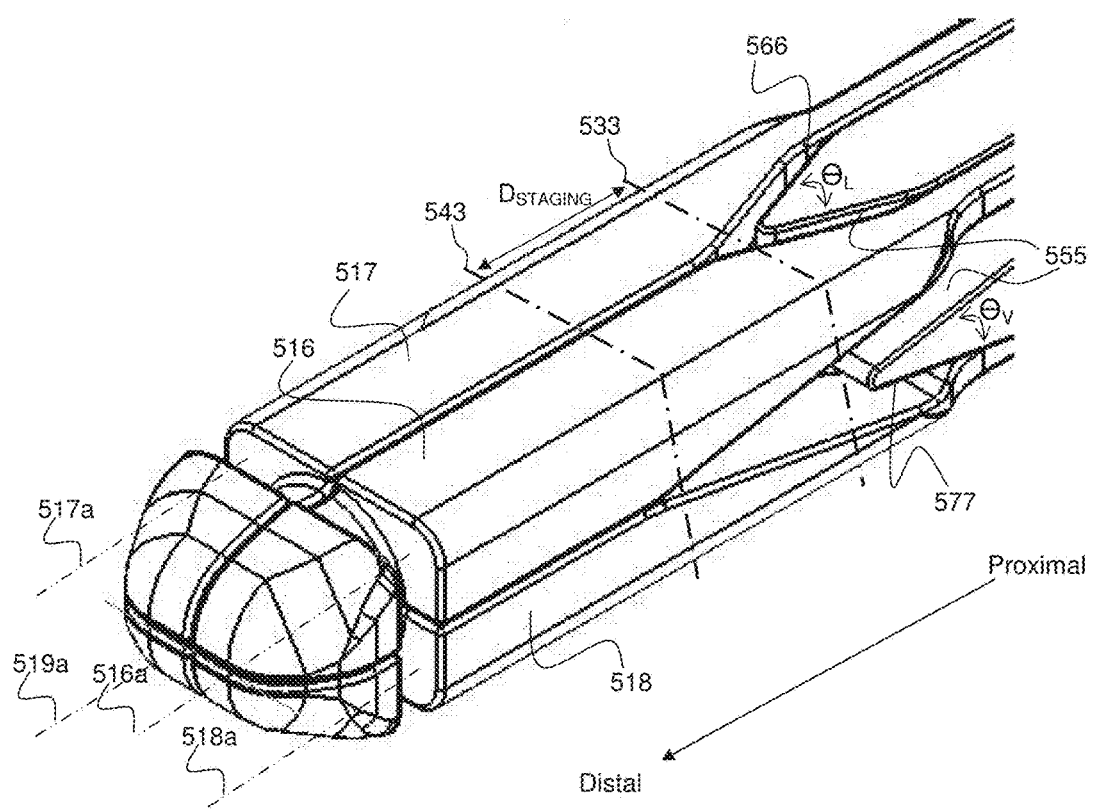
FIG. 5 illustrates the concept of the staged, bilateral expansion of the trial, according to some embodiments.

FIG. 5 illustrates the concept of the staged, bilateral expansion of the trial, according to some embodiments. As shown in FIG. 5, the distance, $D_{STAGING}$, between the onset of the lateral expansion 533 and the onset of the vertical expansion 543 can range from 2 mm to 10 mm, and is the axial proximal-to-distal distance traveled by the shim in the staged expansion.

In some embodiments, the proximal portion of the first top beam and the proximal portion of the first bottom beam can be configured to complement the first side wedge during the proximal-to-distal axial translation for the vertical expansion; and, the proximal portion of the second top beam and the proximal portion of the second bottom beam can be configured to complement the second side wedge during the proximal-to-distal axial translation for the vertical expansion.

In some embodiments, the first top beam 516 can include a proximal portion having an end, a distal portion having an end, and a central axis 516a; the first top beam 516 configured for contacting a first top chamfer 555 (lateral and vertical) of the shim in the expanded state, the central axis 516a of the first top beam 516 at least substantially on (i) a top plane containing the central axis 516a of the first top beam 516 and the central axis 517a of a second top beam 517 and (ii) a first side plane containing the central axis 516a of the first top beam 516 and the central axis 518a of a first bottom beam 518. Likewise, the second top beam 517 can include a proximal portion having an end, a distal portion having an end, and a central axis 517a; the second top beam 517 configured for contacting a second top chamfer 566 (lateral shown, vertical not shown) of the shim in the expanded state, the central axis 517a of the second top beam 517 at least substantially on (i) the top plane and (ii) a second side plane containing the central axis 517a of the second top beam 517 and the central axis 519a of a second bottom beam 519. Likewise, the first bottom beam 518 can include a proximal portion having an end, a distal portion having an end, and a central axis 518a; the first bottom beam 518 configured for contacting a first bottom chamfer 577 (vertical shown, lateral not shown) of the shim in the expanded state, the central axis 518a of the first bottom beam 518 at least substantially on (i) a bottom plane containing the central axis 518a of the first bottom beam 518 and the central axis 517a of a second top beam 517 and (ii) the first side plane. Moreover, the second bottom beam 519 (not shown) can include a proximal portion having an end, a distal portion having an end, and a central axis 519a; the second bottom beam 519 configured for contacting a second bottom chamfer (not shown) of the shim in the expanded state, the central axis 519a of the second bottom beam 519 being at least substantially on (i) the bottom plane and (ii) a second side plane containing the central axis 519a of the second bottom beam 519 and the central axis 517a of the second top beam 517.

In some embodiments, the first top beam can include a proximal portion having an end, a distal portion having an end, and a central axis; the first top beam configured for contacting a first top-lateral surface of the shim and a first top-side surface of the shim in the expanded state, the central axis of the first top beam at least substantially on (i) a top plane containing the central axis of the first top beam and the central axis of a second top beam and (ii) a first side plane containing the central axis of the first top beam and the central axis of a first bottom beam. Likewise, the second top beam can include a proximal portion having an end, a distal portion having an end, and a central axis; the second top beam configured for contacting the second top-lateral surface of the shim and the second top-side surface of the shim in the expanded state, the central axis of the second top beam at least substantially on (i) the top plane and (ii) a second side plane containing the central axis of the second top beam and the central axis of a second bottom beam. Likewise, the first bottom beam can include a proximal portion having an end, a distal portion having an end, and a central axis; the first bottom beam configured for contacting the first bottom-lateral surface of the shim and the first bottom-side surface of the shim in the expanded state, the central axis of the first bottom beam at least substantially on (i) a bottom plane containing the central axis of the first bottom beam and the central axis of a second top beam and (ii) the first side plane. Moreover, the second bottom beam can include a proximal portion having an end, a distal portion having an end, and a central axis; the second bottom beam configured for contacting the second bottom-lateral surface of the shim and the second bottom-side surface of the shim in the expanded state, the central axis of the second bottom beam being at least substantially on (i) the bottom plane and (ii) a second side plane containing the central axis of the second bottom beam and the second top beam.

The selection and arrangement of the wedges and angles can be selected to stage the expansion of the trial in the lateral and vertical directions. In some embodiments, the shim can comprise a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

In some embodiments, the shim can comprise a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

The shell can be formed using any method of construction known to one of skill, for example, multi-component or single unit. In some embodiments, the shell can be a single-unit formed from a single body of material, and the slider-guide, head, and flex rods can be monolithically integral.

In some embodiments, each subhead can have a shape of a rectangular bar with a tapered tip on the outside surface and chamfers on the inner surfaces. The subheads can be located near the corners of the distal end of the trial. When collapsed for insertion, the head can be 6 mm to 9 mm in height by 6 mm to 10 mm in width, in some embodiments. Moreover, the head can expand in some embodiments to 16 mm in height to 16 mm in width. In some embodiments, the head can expand from 6.7 mm to 11 mm in height and from 9 mm 13 mm in width. In some embodiments, the head can expand from 8 mm to 14 mm height and from 9 mm to 13 mm in width. In some embodiments, the length of the head can range from 20 mm to 60 mm, 20 mm to 50 mm, 20 mm to 40 mm, 25 mm to 45 mm, 25 mm to 55 mm, or any range therein increments of 1 mm.

In some embodiments, the trial can have a means for retaining the collapsed state, such as an elastic means. The elastic means can be, for example, a coil spring or an elastic silicone band. The means for retaining can circumscribe the outer circumference of the subheads, and can be further affixed to the assembly using a transverse groove, helping to pull the subheads together when the shim is pulled in the distal-to-proximal direction.

Figure 6:
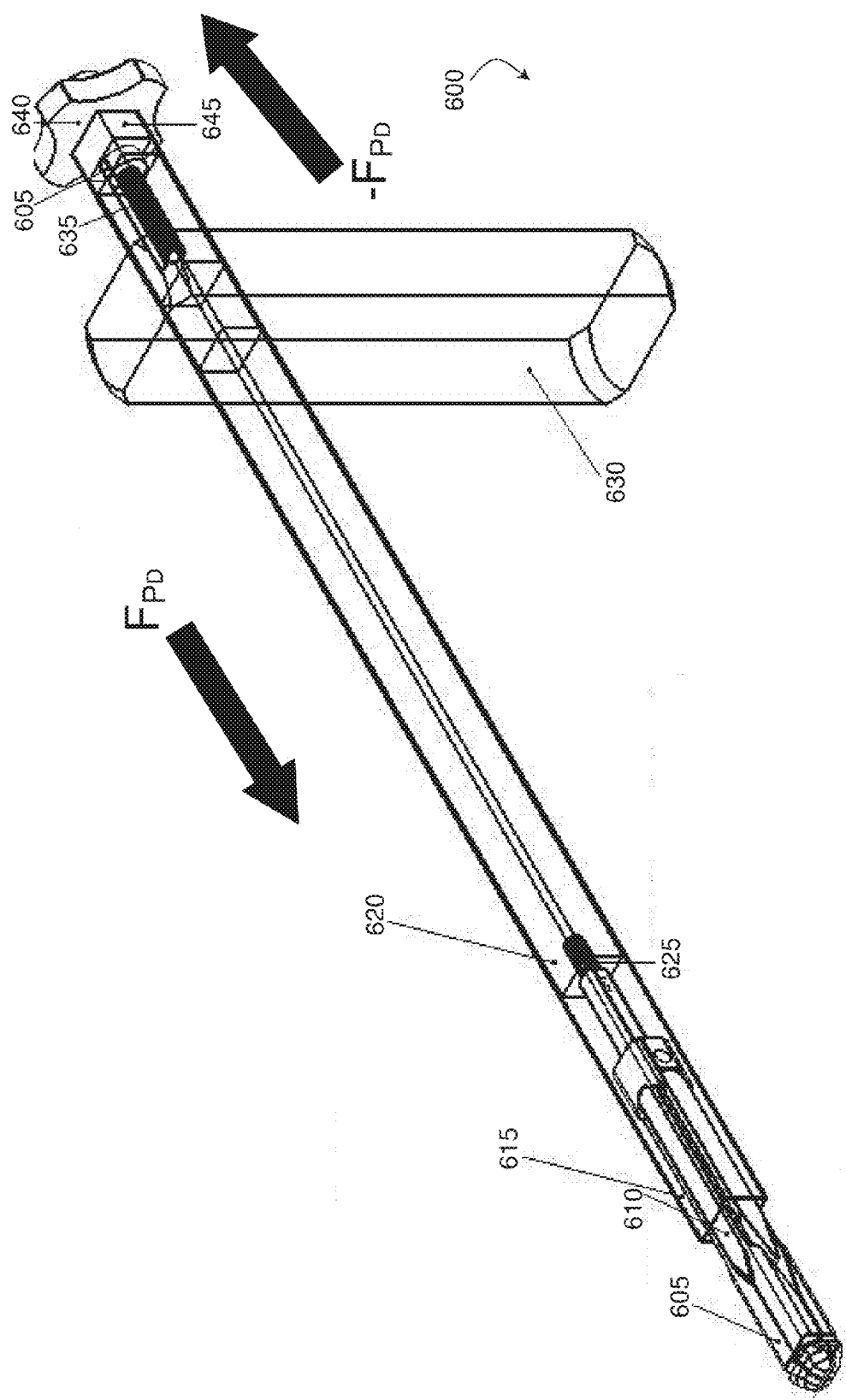
FIG. 6 illustrates a trial system for a staged, bilateral expansion of the trial in an intervertebral space, according to some embodiments.

FIG. 6 illustrates a trial system for a staged, bilateral expansion of the trial in an intervertebral space, according to some embodiments. The trial system 600 includes the trial 605, the shim 610, a guide tube or barrel 615 to help guide the trial 605 into the intervertebral space, an actuation bar 620, a threaded connector 625, a handle 630, an actuator screw 635, an actuator knob 640 to actuate the actuator screw 635 to apply the axial proximal-to-distal force, $F_{PD}$, and a stop block 645 to hold the actuator knob in place against the counter force, $-F_{PD}$.

It should be appreciated that the systems can also include any known means for applying an axial proximal-to-distal force on a shim that expands the trial. In some embodiments, the proximal end of the shim can be configured to receive the axial proximal-to-distal force through the actuation bar for the axial translation, the actuation bar having a proximal portion with a proximal end, a distal portion with a distal end, and configured to transfer the axial proximal-to-distal force to the shim through the slider-guide.

The systems can include such an actuation means operably attached to the proximal end of the actuation bar 620 to transfer the axial proximal-to-distal force $F_{PD}$ to the shim 610 through the distal end of the actuation bar 620. In some embodiments, the actuation bar 620 receives the axial proximal-to-distal force from the actuator screw 635 that can be operably attached to the proximal end of the actuation bar 620 to transfer the force to the shim 619 through the distal end of the actuation bar 620.

Figure 7A:
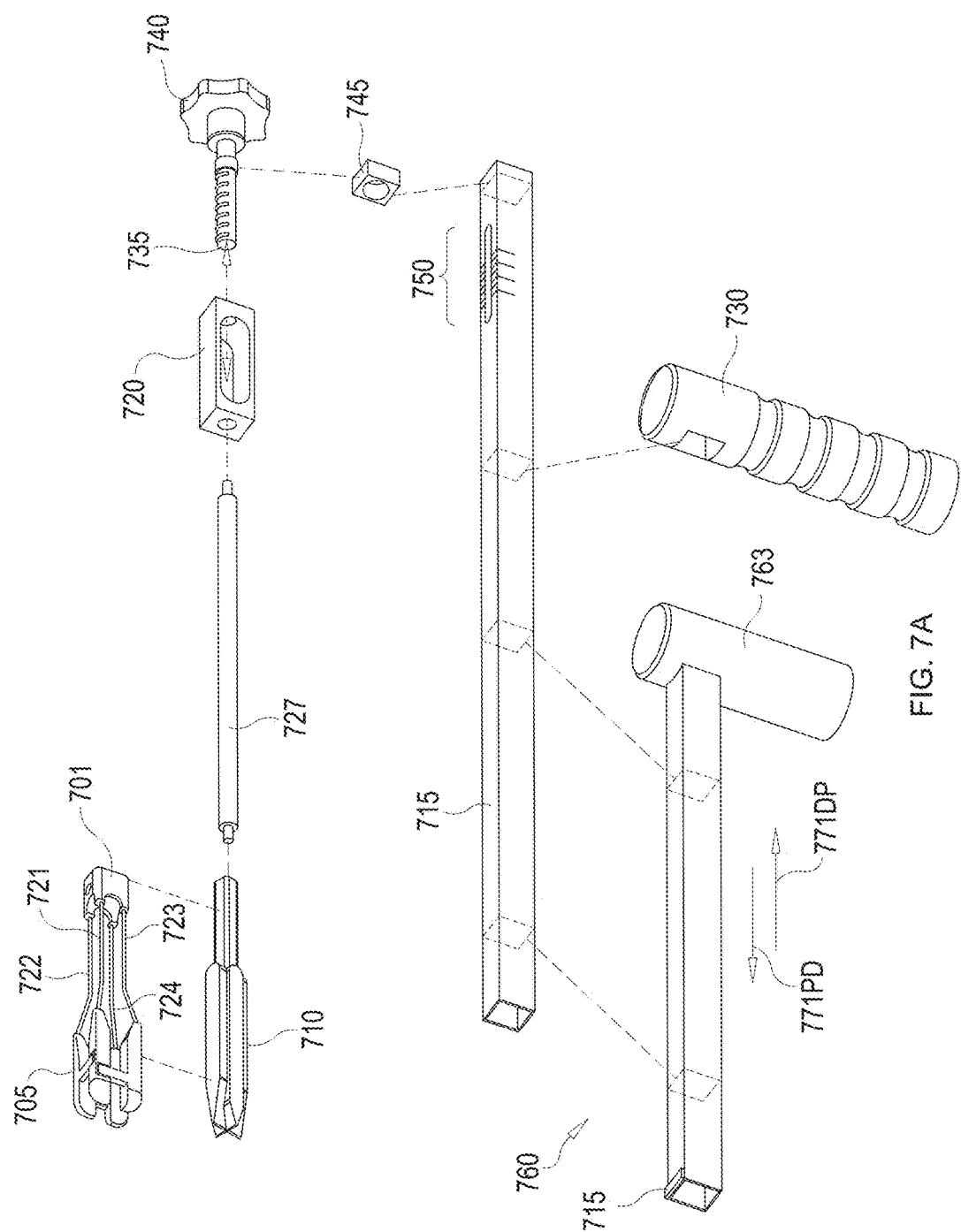
FIGS. 7A and 7B illustrate a trial system with an expansion gauge and a retractable retention plunger for retaining the trial prior to a staged, bilateral expansion of the trial in an intervertebral space, according to some embodiments.
Figure 7B:
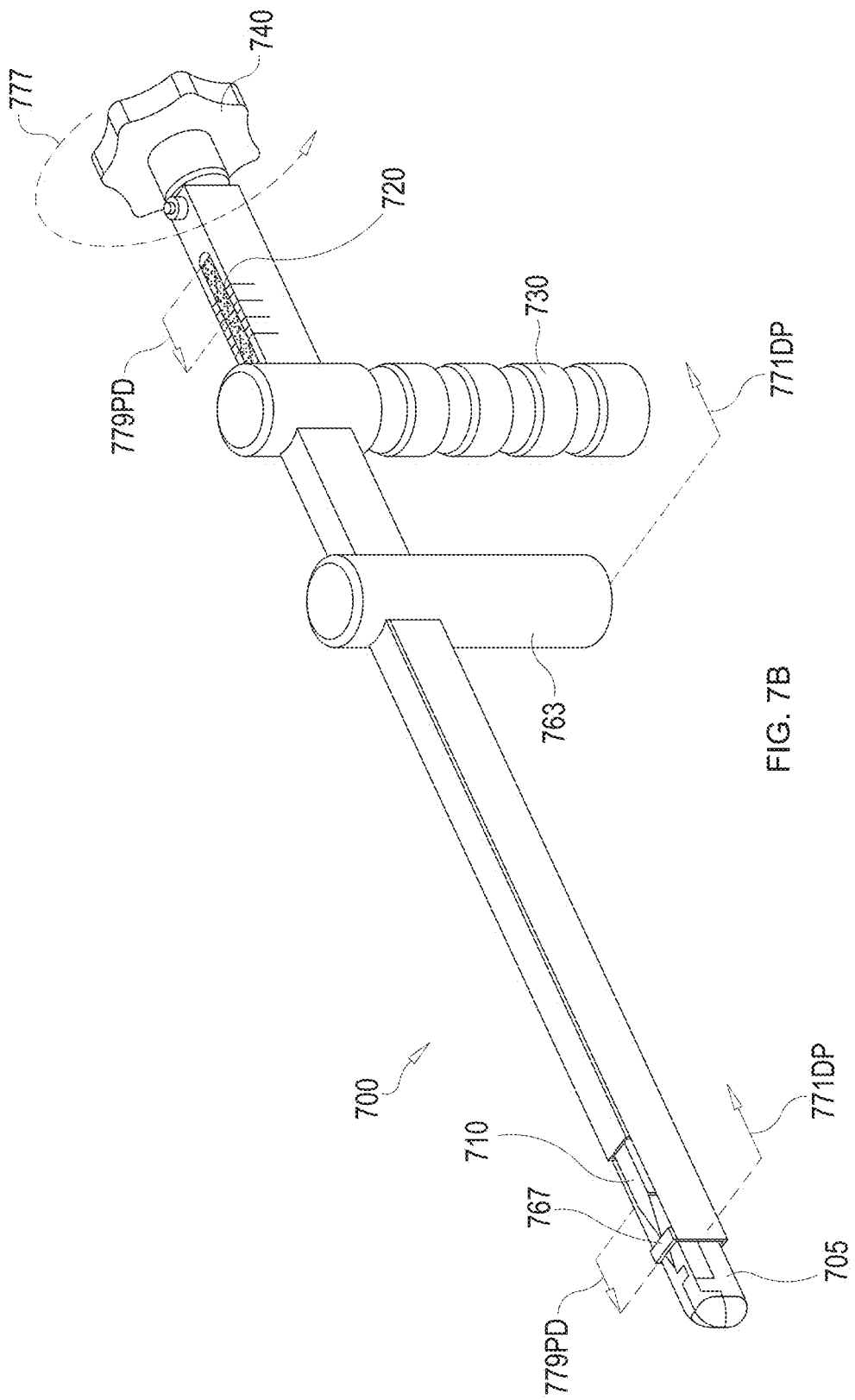

FIGS. 7A and 7B illustrate a trial system with an expansion gauge and a retractable retention plunger for retaining the trial prior to a staged, bilateral expansion of the trial in an intervertebral space, according to some embodiments. FIG. 7A provides an exploded view of the assembly of the system 700. The system 700 includes the trial 705, the shim 710, a guide tube or barrel 715 to help guide the trial 705 into the intervertebral space. The system 700 also includes an actuation bar 720, a push rod 727, a handle 730, an actuator screw 735, an actuator knob 740 to actuate the actuator screw 635 to apply the axial proximal-to-distal force, $F_{PD}$, and a stop block 745 to hold the actuator knob 740 in place against the counter force, $-F_{PD}$.

The systems can further comprise a retractable retention plunger configured for retaining the trial in the collapsed state and releasing the trial for expansion into the expanded state. A retractable retention plunger 760, for example, can also be included with a handle 763 and a retainer 767 for retaining the trial 705 in a collapsed state, the plunger functioning to retain the trial 705 by moving it proximal-to-distal 771PD; and, to release the trial 705 by moving it distal-to-proximal 771DP. The system can also include an expansion gauge 750 to provide a measure of intervertebral expansion and contraction realized when turning 777 the actuator knob 740 clockwise or counterclockwise. The expansion occurs, for example, through an axial proximal-to-distal movement 779PD of the shim 710 into the trial 705. FIG. 7B shows the system assembled with the plunger 760 function to retain the trial 705 in the collapsed state. The trial 705 can be expanded, for example, by pulling the plunger handle 763 in a distal-to-proximal direction for a distal-to-proximal movement 771DP of the retainer 767 to release the trial 705 for the expansion. The expansion is then obtained by turning the knob 740 to obtain the axial proximal-to-distal movement 779PD of the shim 710 into the trial 705.

One or more beam stabilizers can be included stabilize and/or align the subheads during operation of the device. A beam stabilizer, for example, can slidably translate, such that it is telescopic with respect to one or both subheads between which it is operably attached to stabilize and/or align the relationship between the subheads during operation of the device. In some embodiments, the beams can be stabilized with translatable, telescopic linear guides, such that the linear guide can telescope within itself. For example, the first top beam can be operably connected to the second top beam with a top telescopic beam stabilizer, the first top beam can be operably connected to the second top beam with a top telescopic beam stabilizer, the first top beam can be operably connected to the first bottom beam with a first side telescopic beam stabilizer, the second top beam can be operably connected to the second bottom beam with a second side telescopic beam stabilizer, and the first bottom beam can be operably connected to the second bottom beam with a bottom telescopic beam stabilizer. The beam stabilizer, or at least a portion thereof, can be fixably attached, or monolithically integral to, one or both beams between which it is operably connected or positioned in either a fixed or translatable configuration in the trial.

Given the teachings provided herein, one of skill will appreciate that each subhead can be designed/adapted/configured for an operable connection with interlocking and interconnecting structures that serve to provide alignment and stability between the subhead and a second subhead during expansion and/or collapse of the trial. The transverse interconnection structures are intended to provide stability to the head assembly while at least substantially limiting the movement of the heads to the direction of expansion and/or collapse, such that the relative stability between beams in the trial system during expansion or collapse is improved by at least 10%, 20%, 30%, 40%, 50%, 60%, or 70% over the relative stability between beams in a comparison trial system having the same structure in the absence of the beam stabilizer configuration. For example, both the system and the comparison trial system can each have the same configuration of 4 subheads that include a first top beam, a second top beam, a first bottom beam, and a second bottom beam, each of the beams having a central axis. The desired, stabilized and/or aligned configuration can be, for example, that the central axis of the first top beam is at least substantially on (i) a top plane containing the central axis of the first top beam and the central axis of a second top beam and (ii) a first side plane containing the central axis of the first top beam and the central axis of a first bottom beam. If the comparison trial system deviates from the desired stabilized and/or aligned configuration by, for example, 30°, measured as the deviation as the deflection of a beam's central axis from the desired configuration, then an improvement of at least 10% would represent a deflection of 27° or less, an improvement of at least 20% would represent a deflection of 24° or less, an improvement of at least 30% would represent a deflection of 21° or less, an improvement of at least 40% would represent a deflection of 18° or less, an improvement of at least 50% would represent a deflection of 15° or less, an improvement of at least 60% would represent a deflection of 12° or less, an improvement of at least 70% would represent a deflection of 9° or less, an improvement of at least 80% would represent a deflection of 6° or less, an improvement of at least 90% would represent a deflection of 3° or less, an improvement of at least 95% would represent a deflection of 1.5° or less, in some embodiments. One of skill will appreciate that this is merely an example of how the % improvement can be calculated. The same, or any similar, approach can be used as a relative measure of improvement due to configurations that include one or more beam stabilizers.

In some embodiments, the beam stabilizer can be a telescoping male/female relationship between two bosses, a male boss configured on a first beam and a female boss configured on a second beam. In these embodiments, the male boss is monolithically integral to the first beam, and the female boss is monolithically integral to the second beam, the male boss slidably translating with the female boss to at least substantially confining movement between the first beam and the second beam to the transverse movement of expansion and collapse between the beams.

Figure 8:
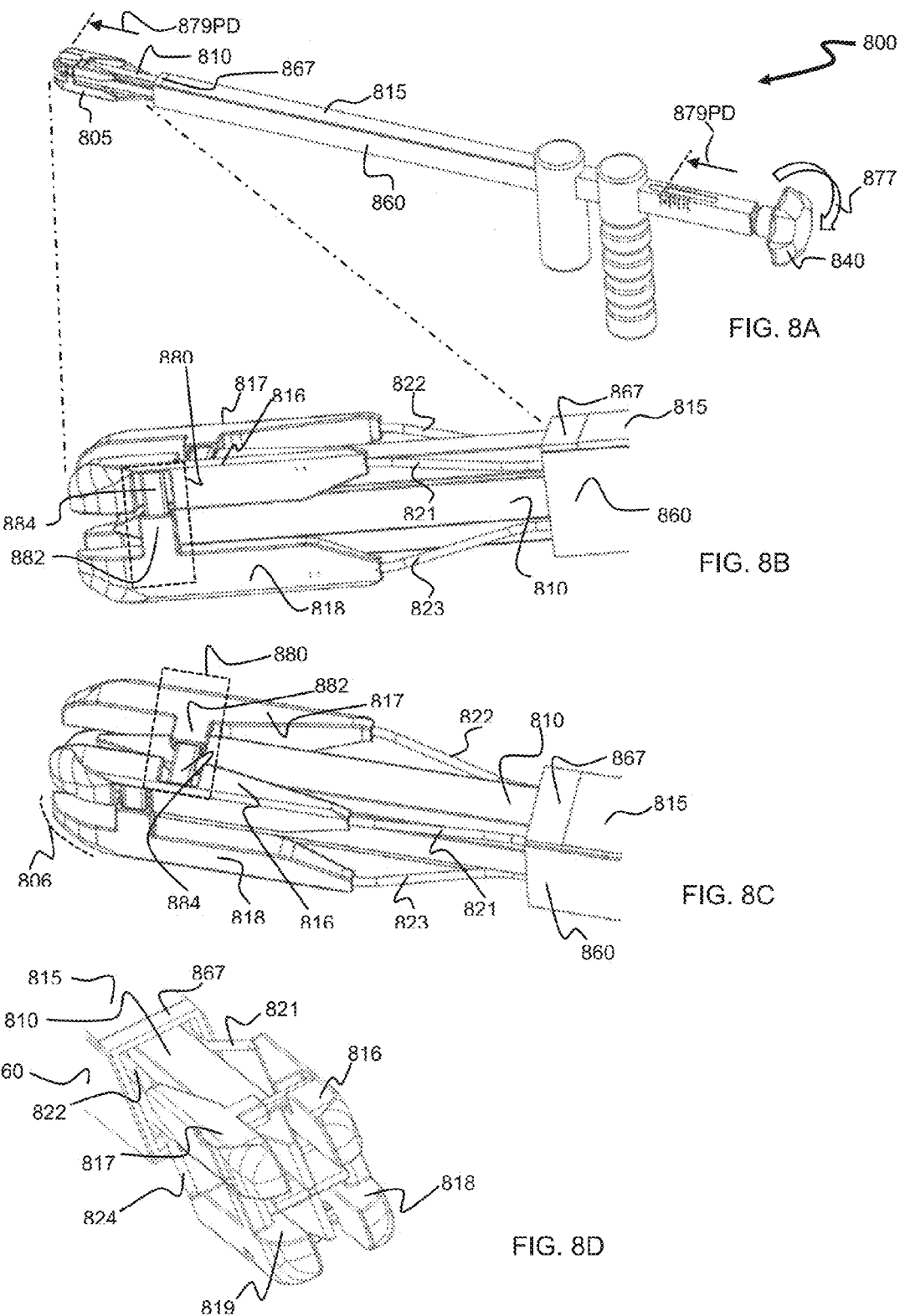
FIGS. 8A-8D illustrate a staged, bilaterally-expandable trial with beam stabilizers that telescope within themselves, according to some embodiments.

FIGS. 8A-8D illustrate a staged, bilaterally-expandable trial with beam stabilizers, according to some embodiments. As shown in FIG. 8A, a system such as system 700 can be used, having the guide tube or barrel 815, plunger 860, and retainer 867, the trial 805 being in the expanded state by turning the knob 840 to obtain the axial proximal-to-distal movement 879PD of the shim 810 into the trial 805. As shown in FIGS. 8B and 8C, a beam stabilizer 880 can be used to provide a means for an increased relative stability between beams that frame the top, bottom, first side, and second side of the trial 805. Such means for providing the increased relative stability between beams can be, for example, a telescopic linear guide configuration having a guide 882 and slider 884. The shim 810 is forced to enter the trial 805 through proximal-to-distal axial movement 879PD, and the beam stabilizers 880 increase the relative stability of the trial during the distraction procedure.

In some embodiments, the telescopic linear guide comprises a slider and a guide. In some embodiments, the slider can be a plate, and the guide can be a rail. In some embodiments, the slider can be plate, and the guide can be a member that at least partially circumscribes the plate. In some embodiments, the slider can be a plate, and the guide can be a cylinder. It should be appreciated that the guide can be a circular cylinder, an elliptical cylinder, a square cylinder, a rectangular cylinder, a triangular cylinder, a pentagonal cylinder, or hexagonal cylinder. Likewise the slider can be any complementary rigid structure, such as a cylindrical rod, an elliptical rod, a square rod, a rectangular rod, a triangular rod, a pentagonal rod, or a hexagonal rod. In some embodiments, the beam stabilizer is an assembly that telescopes to facilitate the expansion and the collapse of the trial. In some embodiments, the slider and the guide translate relative to one another to provide the telescopic movement for expansion and collapse of the trial without a relative rotary motion between the guide and slider.

As shown in FIGS. 8B-8D, the system trial 805 can have a bilaterally-expandable system of 4 subheads 816,817,818, 819 that include a first top beam 816, a second top beam 817, a first bottom beam 818, and a second bottom beam 819. The mid-region can have 4 flex rods 821,822,823,824 that include a first top flex rod 821, a second top flex rod 822, a first bottom flex rod 823, and a second bottom flex rod 824, each of which operably attaches a slider-guide not shown (see, for example, FIG. 3, 310; and FIG. 7, 701) to it's respective subhead. As shown in FIG. 8C, each end 806 of the 4 subheads 816,817,818,819 can be tapered or otherwise round, configured in the collapsed state in some embodiments, for example, as a bullet-nosed tip to avoid damage to the inner annulus during the distraction procedure.

In some embodiments, a pin can be rigidly connected to each of two subheads but telescoping within itself, for example, a first portion of the pin can be hollow to guide a second portion of the pin to slidably translate the second portion as a slider within the guide of the first portion. In some embodiments, the telescoping arrangement of the beam stabilizers can include a linear connector pin, or other single unit linear member (cylindrical rod, elliptical rod, triangular rod, square rod, rectangular rod, trapezoidal rod, pentagonal rod, hexagonal rod, heptagonal rod, octagonal rod, and any other polygonal rod or cylinder) having two ends, each end of which is adapted for operably connecting to a counter-bore hole in one of two subheads between which the pin is positioned and/or connected.

Figure 9A:
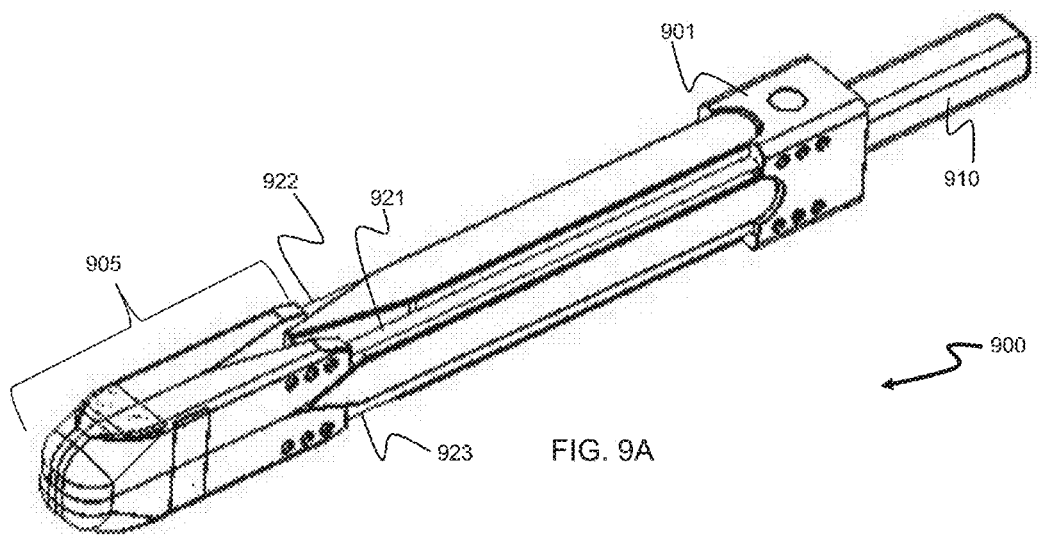
FIGS. 9A-9D illustrate a staged, bilaterally-expandable trial with beam stabilizers that telescope with one or both subheads having a counter-bore, according to some embodiments.
Figure 9B:
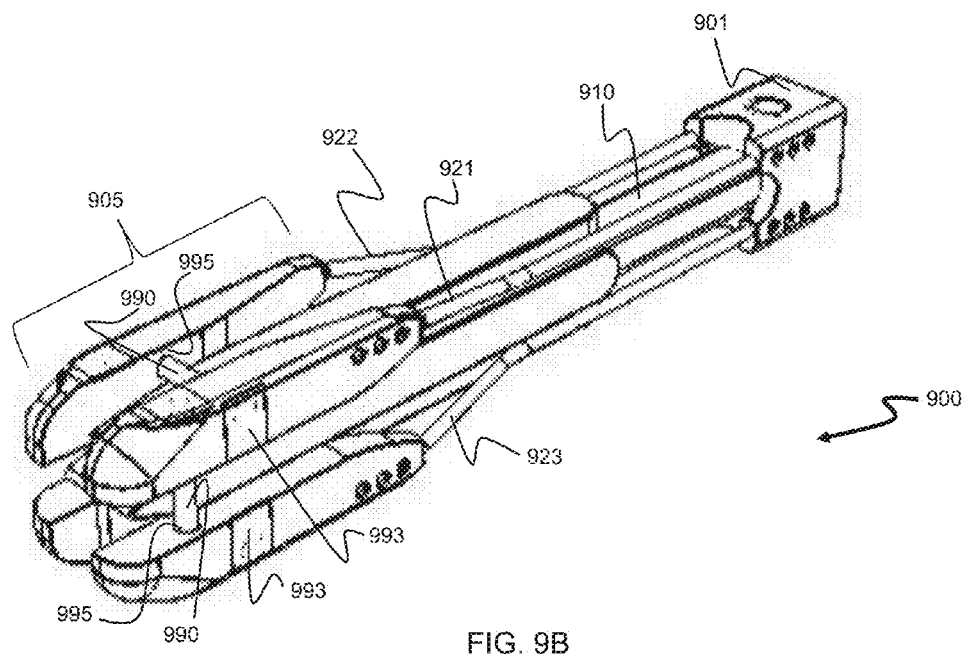
Figure 9C:
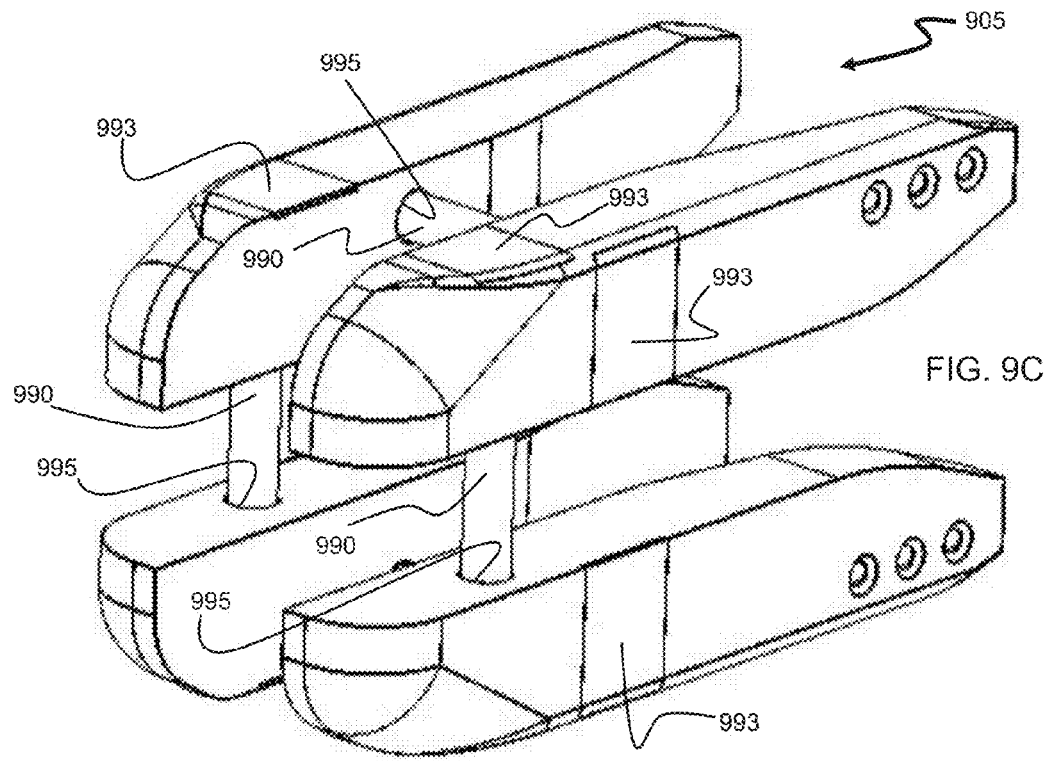

FIGS. 9A-9D illustrate a staged, bilaterally-expandable trial with beam stabilizers that telescope with one or both subheads having a counter-bore, according to some embodiments. As shown in FIGS. 9A (collapsed configuration) and 9B (expanded configuration), the system trial 905 can have a bilaterally-expandable system of 4 subheads 916,917,918, 919 that include a first top beam 916, a second top beam 917, a first bottom beam 918, and a second bottom beam 919. The mid-region can have 4 flex rods 921,922,923,924 that include a first top flex rod 921, a second top flex rod 922, a first bottom flex rod 923, and a second bottom flex rod 924, each of which operably attaches a slider-guide 901 to it's respective subhead. As shown in FIG. 9C (head-only, expanded), each end 906 of the 4 subheads 916,917,918,919 can be tapered or otherwise round, configured in the collapsed state in some embodiments, for example, as a bullet-nosed tip to avoid damage to the inner annulus during the distraction procedure.

Figure 9D:
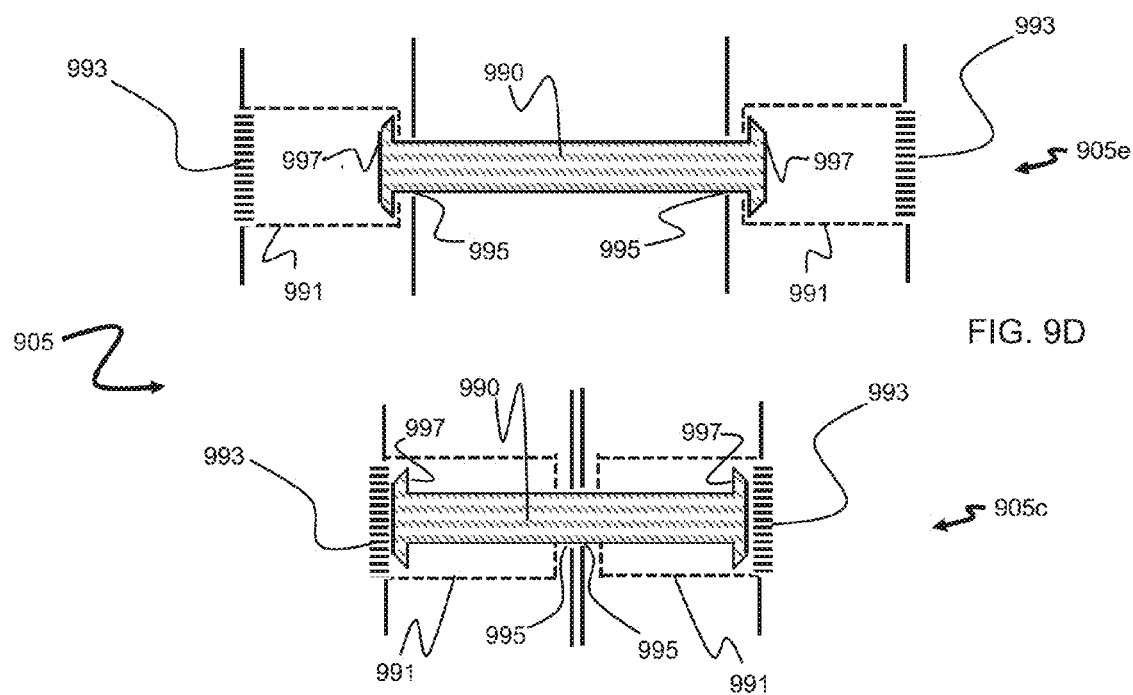

As the head expands as shown in FIGS. 9A-9C, the subhead of trial 905 can slide on a pin 990 transversely while limited in movement by a means (not visible) of stopping the translational expansion. For example, as shown in FIG. 9D each end of the pin 990 can have a retention head, or pinhead 997 that is retained in the counter-bore 991 of each subhead of trial 905 by a cap 993 that covers the counter-bore (not visible) to retain the pin 990 upon expansion 905e and collapse 905c of the trial 905. One of skill will appreciate that in order for the pin 990 to translate in the subhead of the trial 905 and be retained, (i) the outer diameter, or transverse dimension, of the pin 990 is less than the inner diameter, or transverse dimension, of the counter-bore pin guide 995; and (ii) the outer diameter, or transverse dimension, of the pinhead 997 is greater than the inner diameter, or transverse dimension, of the counter-bore pin guide 995. It should also be appreciated that the pinhead 997 can be a cap, a flange, or any other configuration that results in the pinhead 997 having a larger diameter or transverse dimension than the pin 990 and the inner diameter, or transverse dimension, of the counter-bore pin guide 995.

Accordingly, a method of distracting an intervertebral space using the trials is provided. In some embodiments, the method can comprise creating a point of entry into an intervertebral disc, the intervertebral disc having a nucleus pulposus surrounded by an annulus fibrosis, and the point of entry having the maximum lateral dimension created through the annulus fibrosis. The methods can include removing the nucleus pulposus from within the intervertebral disc through the point of entry, leaving the intervertebral space for expansion of the head of the trial within the annulus fibrosis, the intervertebral space having the top vertebral plate and the bottom vertebral plate. The methods can include inserting the head in the collapsed state through the point of entry into the intervertebral space; and, distracting the intervertebral space using a staged, bilateral expansion that includes a first stage and a second stage. The distracting can include a first stage and a second stage, the first stage including expanding the head laterally toward the peripheral zones of the top vertebral plate and the bottom vertebral plate; and, the second stage including expanding the head vertically to distract the intervertebral space, the pressure for the expansion occurring preferably, and at least primarily, at or near the peripheral zones of the top vertebral plate and the bottom vertebral plate. In some embodiments, the lateral dimension of the point of entry ranges from about 5 mm to 18 mm, 6 mm to 18 mm, 7 mm to 18 mm, 5 mm to 15 mm, 5 mm to 16 mm, 5 mm to 17 mm, or any range therein in increments of 1 mm.

In some embodiments, the distracting includes selecting an amount of lateral expansion independent of an amount of vertical expansion. And, in some embodiments, the distracting includes measuring the amount of lateral expansion independent of the amount of vertical expansion.

In some embodiments, the distracting includes as a first stage of lateral expansion, inserting a top wedge into the head between the first top beam and the second top beam, the top wedge composing a portion of the shim and configured to laterally-expand the first top beam away from the second top beam; and, inserting a bottom wedge into the head between the first bottom beam and the second bottom beam, the bottom wedge configured to laterally-expand the first bottom beam away from the second bottom beam. And, as a second stage of expansion, inserting a first side wedge into the head between the first top beam and the first bottom beam, the first side wedge configured to laterally-expand the first top beam away from the first bottom beam; and, inserting a second side wedge into the head between the second top beam and the second bottom beam, the second side wedge configured to laterally-expand the second top beam away from the second bottom beam.

In some embodiments, the distracting includes selecting a shim having a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

In some embodiments, the distracting includes selecting a shim having a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

In some embodiments, the head of the trial can also be used as a "trial shim" for a bilaterally expandable cage by expanding the trial bilaterally and measuring the size of the expanded head to obtain a measure of the width and the height of the intervertebral space.

One of skill will appreciate that the teachings provided herein are directed to basic concepts that can extend beyond any particular embodiment, embodiments, figure, or figures. As such, there are several equivalents that can be contemplated having substantially the same function, performed in substantially the same way, for substantially the same result. As such, it should be appreciated that any examples are for purposes of illustration and are not to be construed as otherwise limiting to the teachings. For example, it should be appreciated that the devices provided herein can also be used in other areas of the body, and can have slightly varying configurations and adaptations. The devices provided herein can be used, for example, in intravertebral body procedures to distract intervertebral bodies in operations that may include the repair of, for example, collapsed, damaged or unstable vertebral bodies suffering from disease or injury.

We claim:

1. A staged, bilaterally-expandable trial for an intervertebral space, comprising:
   a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state; and,
   a shim configured for a proximal-to-distal axial translation in the lumen of the shell that induces a lateral force on the 4 subheads and a vertical force on the 4 subheads;
   wherein the shim has
   a top wedge and a bottom wedge, each configured to laterally-expand the subheads;
   a first side wedge and a second side wedge, each configured to vertically-expand the subheads;
   the shim is configured to induce a lateral expansion followed by a vertical expansion; and,
   the distance, $D_{STAGING}$, of the axial translation between the onset of the lateral expansion and the onset of the vertical translation ranges from 2 mm to 10 mm.

2. A staged, bilaterally-expandable trial for an intervertebral space, comprising:
   a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state; and,
   a shim configured for a proximal-to-distal axial translation in the lumen of the shell that induces a lateral force on the 4 subheads and a vertical force on the 4 subheads;
   wherein the shim comprises a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

3. A staged, bilaterally-expandable trial for an intervertebral space, comprising:
   a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state; and,
   a shim configured for a proximal-to-distal axial translation in the lumen of the shell that induces a lateral force on the 4 subheads and a vertical force on the 4 subheads;
   wherein the wherein the shim comprises a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

4. A system for distracting an intervertebral space, the system comprising
   a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state;
   a shim configured for a proximal-to-distal axial translation in the lumen of the shell that induces a lateral force on the 4 subheads and a vertical force on the 4 subheads;
   an actuation bar, the actuation bar having a proximal portion with a proximal end, a distal portion with a distal end, and configured to transfer the axial proximal-to-distal force to the shim through the slider-guide; the shim configured to receive an axial proximal-to-distal force through the actuation bar for the axial translation; and,
   an actuation means operably attached to the proximal end of the actuation bar to transfer the axial proximal-to-distal force to the shim through the distal end of the actuation bar;

wherein the shim has
a top wedge and a bottom wedge, each configured to laterally-expand the subheads;
a first side wedge and a second side wedge, each configured to vertically-expand the subheads;
the shim is configured to induce a lateral expansion followed by a vertical expansion; and,
the distance, $D_{STAGING}$, of the axial translation between the onset of the lateral expansion and the onset of the vertical translation ranges from 2 mm to 10 mm.

5. A system for distracting an intervertebral space, the system comprising
a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state;
a shim configured for a proximal-to-distal axial translation in the lumen of the shell that induces a lateral force on the 4 subheads and a vertical force on the 4 subheads;
an actuation bar, the actuation bar having a proximal portion with a proximal end, a distal portion with a distal end, and configured to transfer the axial proximal-to-distal force to the shim through the slider-guide; the shim configured to receive an axial proximal-to-distal force through the actuation bar for the axial translation; and,
an actuation means operably attached to the proximal end of the actuation bar to transfer the axial proximal-to-distal force to the shim through the distal end of the actuation bar;
wherein the shim comprises a lateral-expansion wedge with angle $\theta_L$ ranging from 10° to 30° and a vertical-expansion wedge with angle $\theta_V$ ranging from 30° to 50°, the apex of the lateral-expansion wedge and the apex of the vertical-expansion wedge each at least substantially on a single plane that is orthogonal to the central axis of the shim, and the ratio of $\theta_V:\theta_L$ ranges from 1:1.25 to 1:4 to stage the bilateral expansion of the head.

6. A system for distracting an intervertebral space, the system comprising
a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state;
a shim configured for a proximal-to-distal axial translation in the lumen of the shell that induces a lateral force on the 4 subheads and a vertical force on the 4 subheads;
an actuation bar, the actuation bar having a proximal portion with a proximal end, a distal portion with a distal end, and configured to transfer the axial proximal-to-distal force to the shim through the slider-guide; the shim configured to receive an axial proximal-to-distal force through the actuation bar for the axial translation; and,
an actuation means operably attached to the proximal end of the actuation bar to transfer the axial proximal-to-distal force to the shim through the distal end of the actuation bar;
wherein the shim comprises a lateral-expansion wedge with angle $\theta_L$ ranging from 10° to 90° and a vertical-expansion wedge with angle $\theta_V$ ranging from 10° to 90°, the apex of the lateral-expansion wedge on a first plane and the apex of the vertical expansion wedge on a second plane, both the first plane and the second plane being orthogonal to the central axis of the shim and separated on the central axis at a distance ranging from 2 mm to 10 mm to stage the bilateral expansion of the head.

7. The trial of claim 1, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

8. The trial of claim 1, wherein the shell is a single-unit formed from a single body of material, and the slider-guide, head, and flex rods are monolithically integral.

9. The trial of claim 1, wherein each subhead is operably connected to an adjacent subhead with a telescopic beam stabilizer.

10. The system of claim 4, each subhead is operably connected to an adjacent subhead with a telescopic beam stabilizer.

11. The system of claim 4, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

12. The system of claim 4, wherein the shell is a single-unit formed from a single body of material, and the slider-guide, head, and flex rods are monolithically integral.

13. A method of distracting an intervertebral space, the method comprising:
using a staged, bilaterally-expandable trial for an intervertebral space, comprising:
a bilaterally-expandable shell having a bilaterally-expandable head with 4 subheads, 4 flex rods, a slider guide, and a lumen, each of the 4 subheads operably connected to a respective flex rod, each of which operably attaches the slider-guide to it's respective subhead, the shell having a collapsed state and an expanded state; and,
a shim configured for a proximal-to-distal axial translation in the lumen of the shell that induces a lateral force on the 4 subheads and a vertical force on the 4 subheads;
creating a point of entry into an intervertebral disc, the intervertebral disc having a nucleus pulposus surrounded by an annulus fibrosis, and the point of entry having the maximum lateral dimension created through the annulus fibrosis;

removing the nucleus pulposus from within the intervertebral disc through the point of entry, leaving the intervertebral space for expansion of the head of the trial of claim 1 within the annulus fibrosis, the intervertebral space having the top vertebral plate and the bottom vertebral plate;

inserting the head in the collapsed state through the point of entry into the intervertebral space; and, distracting the intervertebral space using a staged, bilateral expansion that includes a first stage and a second stage, the first stage including expanding the head laterally toward the peripheral zones of the top vertebral plate and the bottom vertebral plate; and, the second stage including expanding the head vertically to distract the intervertebral space.

14. The method of claim 13 further comprising retaining the trial with a retractable retention plunger and retracting the plunger to expand the trial.

15. The method of claim 13, wherein the lateral dimension of the point of entry ranges from about 5 mm to about 18 mm.

16. The method of claim 13, wherein the distracting includes selecting an amount of lateral expansion independent of an amount of vertical expansion.

17. The method of claim 13, wherein the distracting includes measuring the amount of lateral expansion independent of the amount of vertical expansion.

18. The trial of claim 2, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

19. The trial of claim 3, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

20. The trial of claim 2, wherein the shell is a single-unit formed from a single body of material, and the slider-guide, head, and flex rods are monolithically integral.

21. The trial of claim 3, wherein the shell is a single-unit formed from a single body of material, and the slider-guide, head, and flex rods are monolithically integral.

22. The trial of claim 2, wherein each subhead is operably connected to an adjacent subhead with a telescopic beam stabilizer.

23. The trial of claim 3, wherein each subhead is operably connected to an adjacent subhead with a telescopic beam stabilizer.

24. The system of claim 5, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

25. The system of claim 6, wherein
the head has
a transverse cross-section in the collapsed state having a maximum dimension ranging from 5 mm to 18 mm for placing the frame in an intervertebral space through an annular opening for expansion in the intervertebral space; and,
a transverse cross-section in the expanded state having a maximum dimension ranging from 6.5 to 28 mm in the intervertebral space;
and,
the shim has a transverse cross-section with a maximum dimension ranging from 5 mm to 18 mm for translating the shim in the lumen of the shell.

26. The system of claim 5, wherein the shell is a single-unit formed from a single body of material, and the slider-guide, head, and flex rods are monolithically integral.

27. The system of claim 6, wherein the shell is a single-unit formed from a single body of material, and the slider-guide, head, and flex rods are monolithically integral.

28. The system of claim 5, each subhead is operably connected to an adjacent subhead with a telescopic beam stabilizer.

29. The system of claim 6, each subhead is operably connected to an adjacent subhead with a telescopic beam stabilizer.

* * * * *